United States Patent [19]
Gray et al.

[11] Patent Number: 5,856,103
[45] Date of Patent: Jan. 5, 1999

[54] METHOD FOR SELECTIVELY RANKING SEQUENCES FOR ANTISENSE TARGETING

[75] Inventors: Donald M. Gray, Richardson; Chris L. Clark, Plano, both of Tex.

[73] Assignee: Board of Regents The University of Texas, Austin, Tex.

[21] Appl. No.: 808,474

[22] Filed: Mar. 3, 1997

Related U.S. Application Data

[63] Continuation-in-part of Ser. No. 320,507, Oct. 7, 1994, abandoned.
[51] Int. Cl.$^6$ ........................................ C12Q 1/68
[52] U.S. Cl. .............................. 435/6; 536/23.1
[58] Field of Search ........................ 435/5, 6; 536/23.1; 514/44

[56] References Cited

PUBLICATIONS

Roberts and Crothers (1992) Science 258:1463–66.
Gray and Ratliff (1975) Biopolymers 14:487–98.
Kiessling et al. (1992) Biochemistry 31:2829–34.
Goldstein and Benight (1992) Biopolymers 32:1679–93.
Gray and Tinoco (1970) Biopolymers 9:223–44.
Agrawal, et al., "Oligodeoxynucleoside phosphoramidates and phosphorothioates as inhibitors of human immunodeficiency virus," *Proc. Natl. Acad. Sci. USA*, 85:7079–7083, 1988.
Agrawal, et al., "Inhibition of human immunodeficiency virus in early infected and chronically infected cells by antisense oligodeoxynucleotides and their phosphorothioate analogues," *Proc. Natl. Acad. Sci. USA*, 86:7790–7794, 1989.
Buck, et al., "Phosphate–Methylated DNA Aimed at HIV–1 RNA Loops and Integrated DNA Inhibits Viral Infectivity," *Science*, 248:208–212, 1990.
Cazenave, et al., "Comparative inhibition of rabbit globin mRNA translation by modified antisense oligodeoxynucleotides," *Nucleic Acids Research*, 17(11), 4255–4273, 1989.
Goodchild, et al., "Inhibition of human immunodeficiency virus replication by antisense oligodeoxynucleotides," *Proc. Natl. Acad. Sci. USA*, 85:5507–5511, 1988.
Gray, Donald M. and Tinoco, Jr., Ignacio, "A New Approach to the Study of Sequence–Dependent Properties of Polynucleotides," *Biopolymers*, 9:223–244, 1970.
Letsinger, et al., "Cholesteryl–conjugated oligonucleotides: Synthesis, properties, and activity as inhibitors of replication of human immunodeficiency virus in cell culture," *Proc. Natl. Acad. Sci, USA*, 86:6653–6556, 1989.

Marcus–Sekura, Carol J., "Techniques for Using Antisense Oligodeoxyribonucleotides to Study Gene Expression," *Analytical Biochemistry*, 172:289–295, 1988.
Matsukura, et al., "Phosphorothioate analogs of oligodeoxynucleotides: Inhibitors of replication and cytopathic effects of human immunodeficiency virus," *Proc. Natl. Acad. Sci. USA* 84:7706–7710, 1987.
Matteucci, Mark D. and Wagner, Richard W., "In pursuit of antisense," *Nature*, 384:20–22, 1996.
Mori, et al., "Phosphoroselenoate oligodeoxynucleotides: synthesis, physico–chemical characterization, anti–sense inhibitory properties and anti–HIV activity," *Nucleic Acids Research*, 17(20):8207–8219, 1989.
Sarin, et al., "Inhibition of acquired immunodeficiency syndrome virus by oligodeoxynucleoside methylphosphonates," *Proc. Natl. Acad. Sci. USA*, 85:7448–7451, 1988.
Shibahara, et al., "Inhibition of human immunodeficiency virus (HIV–1) replication by synthetic oligo–RNA derivatives," *Nucleic Acids Research*, 17 (1):239–253, 1989.
Stein, C.A., and Cohen, Jack S., "Oligodeoxynucleotides as Inhibitors of Gene Expression: A Review," *Cancer Research*, 48:2659–2668, 1988.
Stevenson, Mario, and Iversen, Patrick L., "Inhibition of Human Immunodeficiency Virus Type 1–mediated Cytopathic Effects by Poly(L–lysine)–conjugated Synthetic Antisense Oligodeoxynucleotides," *J. gen Virol*, 70:2673–2682, 1989.
Toulmé, J. –J. and C. Hélène, "Antimessenger oligodeoxyribonucleotides: an alternative to antisense RNA for artificial regulation of gene expression–a review," *Gene*, 72:51–58, 1988.
van der Krol, et al., "Modulation of Eukaryotic Gene Expression by Complementary RNA or DNA Sequences," *BioTechniques*, 6(10):958–975, 1988.
Zaia, et al., "Inhibition of Human Immunodeficiency Virus by Using an Oligonucleoside Methylphosphonate Targeted to the tat–3 Gene," *Journal of Virology*, 62:3914–3917, 1988.

*Primary Examiner*—Scott W. Houtteman
*Attorney, Agent, or Firm*—Denise L. Mayfield

[57] ABSTRACT

A system and method for assessing the minimum number of RNA:DNA sequence combinations whose properties need to be determined for selecting antisense oligonucleotide sequences that will form the most stable hybrid among all those possible in a given target mRNA sequence is provided.

15 Claims, 4 Drawing Sheets

METHOD FOR SELECTIVELY RANKING SEQUENCES FOR ANTISENSE TARGETING

This application is a continuation-in-part of application Ser. No. 08/320,507, now abandoned, filed Oct. 7, 1994.

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present invention generally relates to an apparatus and method for ranking nucleic acid sequences based on stability of nucleic acid oligomer sequence binding interactions to select sequence zones for antisense targeting.

BACKGROUND OF THE INVENTION

It is well known that using the techniques of molecular biology specific sequences may be selected and engineered to modify useful microorganisms to create molecules that may be used for treating cancer, leukemia and HIV-related diseases. Generally, bodily states in mammals, including infectious disease states are directly affected by proteins. Those proteins acting directly or through enzymatic functions contribute in large proportion to many diseases in animals and humans. In the past, therapeutic treatment has focused on interactions with those proteins in an effort to moderate the disease. Attempts have also been made to moderate the actual production of such proteins by interaction with molecules that directly affect their synthesis, i.e., the DNA sequence that underlies the gene product. It is well known that by interfering with the production of the proteins, the effect of the therapeutic results can be maximized. Likewise, therapeutic approaches have been developed that interfere with gene expression, leading to undesired formations which need to be patrolled.

There are numerous methods that have been formulated for inhibiting specific gene expression which have been adopted to some degree and have been defined as antisense nucleic acids. The basic approach is that an oligonucleotide analog complimentary to a specific targeted messenger RNA or mRNA sequence is used. Pertinent references include those of Stein and Cohen (1988); Walder (1988); Marcus-Sekura (1988); Zan (1988); Van der Krol (1988) and Matteucci and Wagner (1996). Each of the foregoing concern general antisense theory and prior techniques.

For example, prior attempts to inhibit HIV gene synthesis by various antisense approaches have been made by a number of researchers. Zamecnik and coworkers have used a transcriptase primer site and splice donor/acceptor sites (P. C. Zamecnik, et al., 1986). Goodchild and coworkers have made phosphodiester compounds targeted to the initiation sites for translation, the cap site, the polyadenylation signal, the 5' repeat region and a site between the gag and pol genes (J. Goodchild, et al., 1988). In the Goodchild study, the greatest activity was achieved by targeting the polyadenylation signal. Agrawal and coworkers have extended the studies of Goodchild by using chemically modified oligonucleotide analogs, which were also targeted to the cap and splice donor/acceptor sites (A. Agrawal, et al., 1988). A portion of one of these oligonucleotide analogs overlapped a portion of the HIV TAR region but was not found to have an exemplary effect. Neither was this oligonucleotide analog designed to interfere with the HIV TAR region. Agrawal and coworkers have used oligonucleotide analogs targeted to the splice donor/acceptor site to inhibit HIV infection in early infected and chronically infected cells (S. Agrawal, et al., 1989).

Sarin and coworkers have also used chemically modified oligonucleotide analogs targeted to the cap and splice donor/acceptor sites (P. S. Sarin, et al., 1988). Zia and coworkers, on the other hand, used an oligonucleotide analog targeted to a splice acceptor site to inhibit HIV (J. A. Zia, et al., 1988). Matsukura and coworkers synthesized oligonucleotide analogs targeted to the initiation of translation of the rev gene mRNA (M. Matsukura, et al., 1987; R. L. Letsinger, et al., 1987; and R. L. Letsinger, et al., 1989). Mori and coworkers used a different oligonucleotide analog targeted to the same region as targeted by Matsukura (K. Mori, et al., 1989). Shibahara and coworkers used oligonucleotide analogs targeted to a splice acceptor site as well as to the reverse transcriptase primer binding site (S. Shibahara, et al., 1989). Letsinger and coworkers synthesized and tested oligonucleotide analogs with conjugated cholesterol targeted to a splice site. Stevenson and Iversen conjugated polylysine to oligonucleotide analogs targeted to the splice donor and the 5'-end of the first exon of the tat gene (Stevenson and Iversen, 1989). Buck and coworkers have recently described the use of phosphate-methylated DNA oligonucleotides targeted to HIV mRNA and DNA (H. M. Buck, et al., 1990). In addition, a U.S. Patent issued to Ecker, has disclosed the use of synthetic oligonucleotides to inhibit the activity of the HIV virus (U.S. Pat. No. 5,166,195). The method utilized, however, lacks in forethought and efficacy.

The need has, therefore, arisen for a systematic method and apparatus for identifying target DNA and RNA sequences in a predictable, logical pattern. Also required is a process that optimizes a ranking of nucleic acid sequences for targeting with antisense oligonucleotides. In addition, there is a long felt need for a means of assessing the thermodynamics and strength of nucleic acid hybridization in sequences that are to be the targets of antisense gene targeting technology in order to efficiently and expeditiously affect their expression.

SUMMARY OF THE INVENTION

The present invention relates to antisense nucleic acid technology that generally prescribes that a synthesized nucleic acid oligomer sequence be bound to a mRNA polymer sequence by the pairing of bases, such as using A, G, C or T for the DNA sequence of bases to target mRNA sequences containing U, C, G or A, respectively. Such pairing results in a duplex helical nucleic acid that is a DNA:RNA double-stranded hybrid containing one deoxyribonucleic acid (DNA) strand and one ribonucleic acid strand (RNA). Since the paired hybrids can affect various cellular processes, such as the translation of an mRNA message into a protein, this invention discloses a method and an apparatus for selectively ranking an antisense oligonucleotide (ASO) to increase the efficacy of the antisense process and to more cost effectively engineer oligonucleotides for targeting specific genetic structures.

In practice, the method generally comprises a data processing system for identifying nucleic acid sequences for antisense oligonucleotide targeting. More specifically, the method uses a control computer that is coupled to a memory system which has within one portion of the memory system the nearest-neighbor nucleic acid pair value data list. The nearest-neighbor nucleic acid pair data list is determined by referring to a set of predetermined nucleic acid nearest-neighbor bond comparisons. In practice, the thermodynamic energies needed for splitting combinations of nearest-neighbor base pairs apart are used to determine the ranking and, thus, the sequence of priority in which the location for antisense pairing is sought. The control computer also obtains, via user input, from a memory system or via modem transfer, a nucleic acid sequence that is the sequence to be analyzed for target sequences. Target sequence, as used herein, refers to a nucleic acid segment that is being targeted for antisense oligonucleotide antigene treatment of cells.

Having obtained the sequence to be analyzed and the nearest-neighbor nucleic acid pair value data list, a program is executed by the control computer. The program contains computer instructions which perform a comparison of said nearest-neighbor nucleic acid pair data list and said nucleic acid sequence.

A unique feature of the execution of the program of the present invention is that it operates by using combinations of nearest-neighbor base pair stabilities, rather that relying on assignments of the individual nearest-neighbor base pair stabilities. It is not generally understood in the field that the thermodynamic data acquired for an array of polymeric or oligomeric sequences are restricted such that thermodynamic values for individual nearest-neighbors simply cannot be extracted and assigned without making a number of assumptions about their interactions.

For polymeric sequences, there are three restrictions on the combinations of any nearest-neighbor value that may be expressed in terms of the nearest-neighbors listed in Table 2, hereinbelow, where N is the number of occurrences of that nearest-neighbor combination in a sequence, as derived by Gray & Tinoco (1970), and the number in the parenthesis is the numerical values of the nearest-neighbor assigned in Table 2, below. The first equation expresses the fact that the number of times an rU:dA pair comes before another type of base pair must equal the number of times it comes after another type of base pair. Equations can be similarly written for rA:dT, rC:dG, and rG:dC base pairs. Since one of the four equations can be derived from the other three, only three are independent restrictions, for example:

1. Restriction on rU:dA base pair:
   N(1)+N(2)+N(3)+N(4)=N(2)+N(6)+N(10)+N(14).
2. Restriction on rA:dT base pair:
   N(5)+N(6)+N(7)+N(8)=N(1)+N(5)+N(9)+N(13).
3. Restriction on rC:dG base pair:
   N(9)+N(10)+N(11)+N(12)=N(3)+N(7)+N(11)+N(15).

The apparatus and method of the present invention maintains these restrictions throughout the comparison of target sequences. Therefore, without ever assigning values of thermodynamic parameters or melting temperatures to individual nearest-neighbors, the thermodynamic data acquired for combinations of polymeric DNA:RNA hybrid sequences can be used to predict the values of other polymeric DNA:RNA hybrid combinations of nearest-neighbors.

The apparatus and method of the present invention relies on, and uses, data for polymeric sequences. In the case of oligomeric sequences that vary in length, for example those of less that 20 nucleotides in length, there are five total constraints on the possible combinations of nearest-neighbors. Again, these constraints make it impossible to assign thermodynamic parameters to individual nearest-neighbors (see below). The present invention can be expanded to use data from such shorter oligomeric sequences, where end effects are important. Therefore, it is possible with expanded data to predict the stabilities of DNA:RNA hybrid sequences of any length.

The steps to be performed are accomplished by a control computer beginning with a step for determining the fraction of each type of nearest-neighbor base pair in each target RNA:ASO-DNA hybrid sequence. The next step in the operation of the present invention is substituting the nearest-neighbor base pair fraction into formulas to determine the fraction of each of the thirteen (13) polymers within contiguous segments of the target nucleic acid sequence. In practice, the formulas used to identify the highest and lowest hybridization temperatures along the length of the target nucleic acid sequence are a summation of the hybridization temperature (or thermodynamic energies) as they relate to the relative base pairings. The fractions are multiplied times the total number of pairings to create a stability ranking to yield the relative hybridization temperatures for potential antisense oligonucleotides. Finally, the different nucleic acid segments for which relative hybridization strength has been determined can be ranked according to hybridization potential. Alternatively, the nucleic acid segments for which relative hybridization based on the nearest-neighbor determination can be ranked by other parameters, such as C+G content.

In addition, the method and apparatus of the present invention also anticipates the use of such a comparison of pairings in order to assess where to bind antigene sequences. When dealing with antigene technology, the antigene oligomer binds to a double-stranded DNA sequence. Although different types of nearest-neighbor base pairs may exist, which create a secondary consideration when assessing the location of binding, the principle that only combinations of nearest-neighbors can be used to predict binding energies is exactly the same as for the prediction of antisense DNA binding energies.

Another embodiment of the present invention is a method for operating a control computer to compile a list of ranked nucleic acid sequences which comprises storing a program and its identifier in a first portion of a memory unit of the control computer. An example of the program to be used is the Nearest-Neighbor Thermal Stability Analysis program (NNTSA). After storing the program in the memory unit of the control computer, the next step is obtaining a nucleic acid sequence, followed by obtaining a list of nearest-neighbor nucleic acid pair values, and finally, obtaining a user-defined nucleic acid segment length value. The nucleic acid segment length value is used to determine the length of the DNA segment to be analyzed. The program analyzes the target sequence in a concatenated fashion in all possible reading frames, as shown in Table 1, hereinbelow. The next step in using the program is to compare the target nucleic acid sequence with the nearest-neighbor nucleic acid pair list based on the user-defined nucleic acid segment length. The final step is calculating a nearest-neighbor value for each overlapping and contiguous length of the target nucleic acid sequence of said user-defined nucleic acid segment length to obtain a hybridization value for each segment having the user-defined length.

Yet another embodiment of the present invention is a nearest-neighbor comparison compiler stored via storage media. The storage media of the present invention comprises a first plurality of binary values for obtaining a nucleic acid sequence in a first data format, a second plurality of binary values containing a nearest-neighbor nucleic acid pair value list in a second data format, a third plurality of binary values for comparing the nucleic acid sequence and the nearest-neighbor nucleic acid pair value list, and finally, a fourth plurality of binary values for electronically routing the binary values to an output device. Examples of storage media that can be used with the present invention include, but are not limited to: magnetic tape, optical disk, compact disk, hard disk, floppy disk, ferroelectric memory, optical storage, electrically programmable read only memory (EEPROM), flash memory, read only memory (ROM), static random access memory (SRAM), dynamic random access memory (DRAM), ferromagnetic memory, charge coupled devices, smart cards, and like storage media. One example of the third plurality of binary values is the Nearest-Neighbor Thermal Stability Program (NNTSA).

A final embodiment of the present invention is a computer-implemented process for determining the relative hybridization potential of nucleic acid segments. The computer implemented embodiment of the invention comprises, reading a nucleic acid sequence, such as one on a magnetic disk. The next step performed by the computer is that of obtaining a user-defined segment length. Once a user-defined segment length is obtained, the next step is that of separating the nucleic acid sequence into nucleic acid segments based on the user-defined segment length, as described hereinabove. The next step compares the nucleic acid sequence that has been separated into nucleic acid segments to a nearest-neighbor nucleic acid pair value list. The final step is determining a hybridization potential or ranking for each nucleic acid segment from the nearest-neighbor nucleic acid pair value list. This computer-implemented process for determining the relative hybridization potential can be used to obtain a list that ranks hybridization potential based on the nearest-neighbor determination in, for example, a descending order.

BRIEF DESCRIPTION OF THE DRAWINGS

The present invention can be more readily understood by reference to the detailed description, taken in conjunction with the accompanying drawings of which.

Corresponding numerals and symbols in the different figures refer to corresponding parts unless otherwise indicated.

DETAILED DESCRIPTION OF THE PREFERRED EMBODIMENTS

Figure 1:
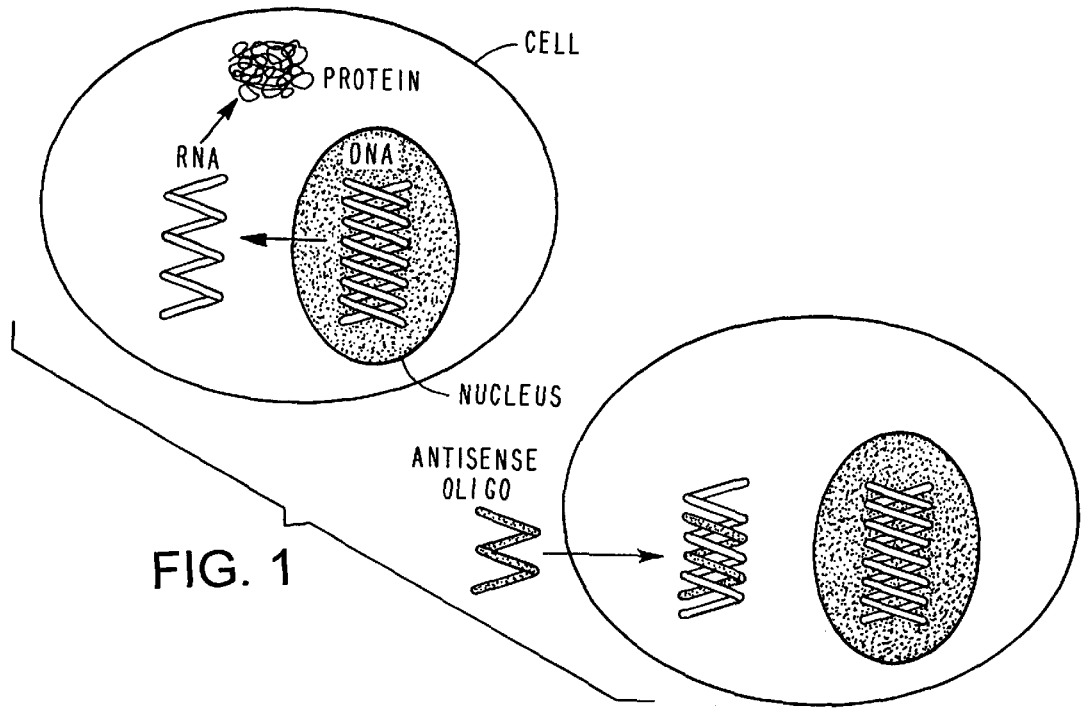
FIG. 1 is an illustration of a system for the synthesis of RNA sequences from DNA, and protein from RNA, and the point of antisense DNA:RNA hybridization.

The present invention relates to an antisense DNA technology which requires the synthesis of DNA oligomer sequences that bind to mRNA polymer sequences by pairing of the bases (A, G, C, or T) of the DNA sequence with the bases (U, C, G, or A, respectively) of the mRNA sequence. Such pairing results in a duplex helical nucleic acid that is a DNA:RNA double-stranded hybrid, containing one deoxyribonucleic acid (DNA) strand and one ribonucleic acid strand (RNA). The paired bases then affect various cellular processes, such as translation of the mRNA message into a protein. The prevention may be by physical blockage of the ribosomes or by other mechanisms such as the degradation of the RNA transcript by RNase H at the site of DNA binding.

To more readily understand the meaning and scope of the present invention, set forth below are some definitions:

DEFINITIONS

ASO and AGO—antisense oligomer (ASO) and antigene oligomer (AGO).

S-ASO—antisense oligomer with phosphorothioate linkages.

Target nucleic acid—molecule of mRNA, of duplex DNA, or of another nucleic acid, the control of which is desired. Such molecules may have 100's or 1000's or more nucleotides or base pairs subunits in a linear array.

Sequence—the order of the nucleotides, usually A, U, G and C for mRNA, usually A, T, C and G, for DNA or the order of base pairs, usually A:T and G:C for duplex DNA within the linear target nucleic acid.

n-mer target sequence—the number of nucleotide or base pair subunits in the entire target nucleic acid, n, is typically more than 20, and n may be larger than 1000.

Target zone—a subsequence within the target nucleic acid. The target zone will typically be about 20 nucleotides long in an mRNA or 20 base pairs long in a duplex DNA.

m-mer target sequence zone—target sequence zone that consists of a subsequence of m nucleotides in a mRNA or m base pairs within the target DNA duplex; m is typically 20. There are n−m+1 target sequence zones within an n-mer target sequence. Each interior m-mer zone overlaps at least one nucleotide or base pair with 2(m−1) other m-mer zones within the target mRNA or duplex DNA.

m-mer ASO—a sequence that is complementary to an m-mer target sequence zone within an mRNA. The base complementarity is typically: A, T, G and C of the ASO pairs with U, A, C and G of the target sequence zone. The ASO can be of any type of normal or modified nucleic acid or peptide or other chemical molecule that has a complementarity to the n-mer target sequence zone.

n-mer AGO—a sequence that is complementary to an m-mer target sequence zone within a duplex DNA. The base complementarity rules depend on the type of triplex that forms. The AGO can be of any type of normal or modified nucleic acid or peptide or other chemical molecule that has a complementarity to the n-mer target sequence zone.

Rank of m-mer target sequence zones or rank of m-mer ASO's or rank of m-mer AGO's—the thermodynamic stability rank is the ΔG free energy, or an approximation to the ΔG, for the reaction "target m-mer zone"+"m-mer ASO or AGO"<->"complex of zone:ASO or zone:AGO," and is the rank of the complex of an m-mer target sequence zone paired together with its complementary m-mer ASO or complementary m-mer AGO sequence. The rank is higher for a more stable complex (more negative ΔG).

Independent model m-mer sequences—A minimum set of sequences, defined as in Gray and Tinoco (1970), whose stability ranks can be used to determine the stability ranks of all possible m-mer target sequence zones and whose stability ranks are referred to herein as the nearest-neighbor nucleic acid pair value data list.

BACKGROUND OF ANTISENSE TECHNOLOGY

The term "antisense" has entered the popular vocabulary as a term denoting a novel approach to chemotherapy which is based upon the complementary pairing of ASO nucleic acids with a target nucleic acid.

The use of such a compound requires a complementarity of the antisense base sequence to a target zone of an mRNA, so that the antisense ASO will bind to that mRNA target sequence and will bring about selective inhibition of gene expression (D. A. Melton, 1988; Stein and Cohen, 1988; and Toulmé and Héléne, 1988). A more thorough understanding of such technology can be found in a book edited by Cohen (Oligonucleotides—Antisense Inhibitors of Gene Expression (1989)), and a recent review by Mercola and Cohen (1995).

Referring to FIG. 1, the schematic representation of the process of transfer of information from the DNA genome to a protein product can be seen. If the gene product (protein) is one whose controlled synthesis is essential for the well-being of the organism or cell, then a defective synthesis or an unwanted protein may lead to illness or death. FIG. 1 also illustrates that an antisense oligonucleotide can be used to inhibit or terminate protein synthesis.

A summary of the relevant portion of the disclosure from the review by J. S. Cohen (Id., 1989, pp. 1–6) is set forth below.

There are five basic assumptions built into this approach:
(1) Cellular uptake: It is assumed that the oligo will cross the cell membrane and will be able to reach its target sequence within the cell.
(2) Stability: The oligo will be stable under in vivo conditions, and will reach the target sequence in significant quantity.
(3) Hybridization: The oligo will hybridize with the target sequence so that a DNA:RNA hybrid will be produced.
(4) Inhibition of expression: The formation of this hybrid will prevent the expression of the gene(s) coded for by the hybridized mRNA.
(5) Selectivity of binding: The oligo will not be bound non-selectively to many other sites, particularly protein sites, and thus have its effective concentration, or potency reduced.

The results of early studies that showed selective inhibition of gene expression in Rous sarcoma virus with a synthetic 13-mer (Zamenik and Stephenson, 1978) indicated that this oligo was indeed penetrating into cells. However, the general resistance to this possibility, and the difficulty in synthesizing oligos of such length until the mid-1980's, certainly held up progress in this area.

Once automated synthesis became possible, it was inevitable that further attempts would be made to test this approach. In order to overcome this supposed problem of cellular uptake of charged oligos, the concept of using chemically modified analogues that are neutral was introduced. These compounds have subsequently been shown to enter cells by passive diffusion. Further studies have culminated recently in the description of a cell-surface receptor for charged oligos that presumably provides a mechanism for them to enter cells.

Initial attempts to inhibit gene expression naturally concentrated on normal oligos with phosphodiester linkages. This led, however, to the criticism that since these compounds are known to be subject to enzymatic hydrolysis by nucleases in vivo and in vitro, these compounds could not form the basis of an effective antisense strategy. This problem of oligo stability could explain the high concentrations of oligos that were found to be required to bring about inhibition of expression in some of the early work. Further, the breakdown of an informational molecule in which the intactness of the base sequence is integral to its mode of action would obviously be a devastating restriction on the strategy of the antisense approach.

Any chemical modification in an oligo can lead to a change in hybridization with its target mRNA sequence at physiological temperature. Since the object of this strategy is to ensure that hybridization occurs, it is mandatory that the hydrogen bonding capability of the bases not be impaired. It is for this reason that the modifications that are made in the oligo are usually in the backbone, and not in the bases or the sugars. Nevertheless, there are many possible modifications of the three portions of the nucleotide unit, only a few of which have so far been investigated. However, in order not to disrupt the formation of Watson-Crick base pairing, it is preferable that any modification that is made should be rather conservative. For example, the substitution of one sulfur atom for any oxygen or phosphate is perhaps the most conservative substitution that can be envisaged that accomplishes the aim of nuclease stability (Eckstein, 1985) without significantly impairing the hybridization of the oligo. The prospect for hybridization of an oligo with a mRNA must also take account of the fact that RNA's can have complex folded tertiary structures and, thus, the target sequence should be contained within a single-stranded accessible region.

The mechanics of inhibition of gene expression were originally presumed to arise from interference of the hybrid DNA:RNA duplex with ribosomal processing. This mechanism has been termed translation arrest or hybridization arrest. However, subsequent work has shown that ribonucleases that hydrolyze such hybrids, namely RNase-H, are actively involved in the mechanism of action (Walder and Walder, 1988). This was shown very clearly by comparison of normal oligos which have the beta configuration of the base—sugar linkage, and non-natural alpha-oligos, which form hybrids with RNA that are not susceptible to RNase-H, and which were concomitantly found not to produce translational arrest (Cavenave, et al., 1989). The most potent antisense effects are obtained when RNA translation is blocked by RNase H cleavage (Matteucci and Wagner, 1996).

It is important for the effectiveness of the antisense oligo approach that the oligo bind selectively to the target complementary sequence. If the oligo is bound non-selectively to the other sites, particularly protein sites that are present in the cell, that would severely limit the potency of any oligo as a putative drug. Eckstein has shown in a series of elegant studies (Eckstein, 1985) that phosphorothioate oligos have a tendency to bind to protein sites and to inhibit nucleases. This "problem" can, in fact, be turned into an advantage if the oligos interact specifically with a protein site, and thus inhibit, for example, a process that is required for vital proliferation. This has been found to be the case with the phosphorothioate analogues which inhibit certain polymerases in a sequence non-specific manner. Such an inhibition cannot be described as an antisense effect. However, the inhibition of HIV reverse transcriptase by phosphorothioate antisense oligomers (S-ASO's) (Matsukura, et al. 1988), and the effectiveness of ASO's that have led to twelve clinical trials (Mercola and Cohen, 1995; Matteucci and Wagner, 1996) which illustrate that phosphorothioates are particularly valuable. This is largely because phosphorothioates retain the ability to activate RNase H.

If RNA is to be regarded as the legitimate target for this novel class of drugs, then much can be done to improve their effectiveness. One of the chief questions that arises is what part of the mRNA to target, for example one might target the 5' initiation codon as one of the preferred sites.

The covalent addition of intercalative or reactive groups onto either the 3' or 5' end of the oligo is already established as an appropriate modification of the antisense approach. In the former case, the intercalator is intended to enhance oligo binding, thus enabling short oligos to be used more effectively. While this would reduce the cost of an oligo, this tactic involves relatively non-selective interaction at the expense of a longer, more selective antisense base sequence. Alkylating agents attached to oligos have been used for chemical modifications of the other strand in a DNA duplex, but can also be adapted for DNA:RNA duplexes. The whole area of attaching hydrolyzing groups to the oligo (Stein and Cohen, 1988) or even ribonucleases (Corey and Schultz, 1987), is still very much in its infancy, although the cellular uptake and antigenicity of such putative oligo-enzymes is clearly a problem that must be addressed.

Figure 2:
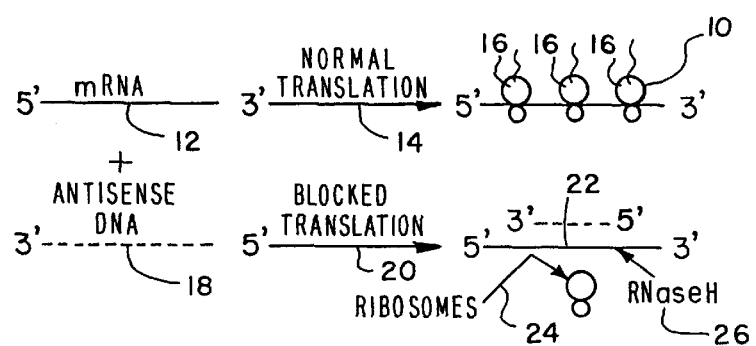
FIG. 2 is a more detailed illustration of blocked protein synthesis using an antisense oligomer.

Referring to FIG. 2, a system for translation of mRNA is illustrated. More specifically, an mRNA polymer sequence 12 generally is acted on by ribosome machinery 10 such that if normal translation 14 occurs then nascent polypeptides 16 will readily be formed to give a sequence of amino acids. Conversely, if the mRNA binds an antisense DNA oligomer (ASO) sequence 18, a blocked translation 20 occurs, either because ribosomes 24 cannot translate or because RNase H 26 cleaves at the hybrid sequence 22. The antisense oligomer generally must be DNA, instead of RNA, since RNase H only attacks the RNA strand of DNA:RNA hybrids. Many chemical modifications of the antisense oligomer are possible, such as the substitution of phosphates in the sugar-phosphate linkages with phosphorothioate linkages. Set forth below is an illustration of the unmodified phosphate linkage and the phosphorothioate linkage.

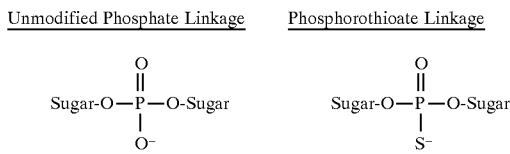

Computer Control Apparatus and System

Figure 3:
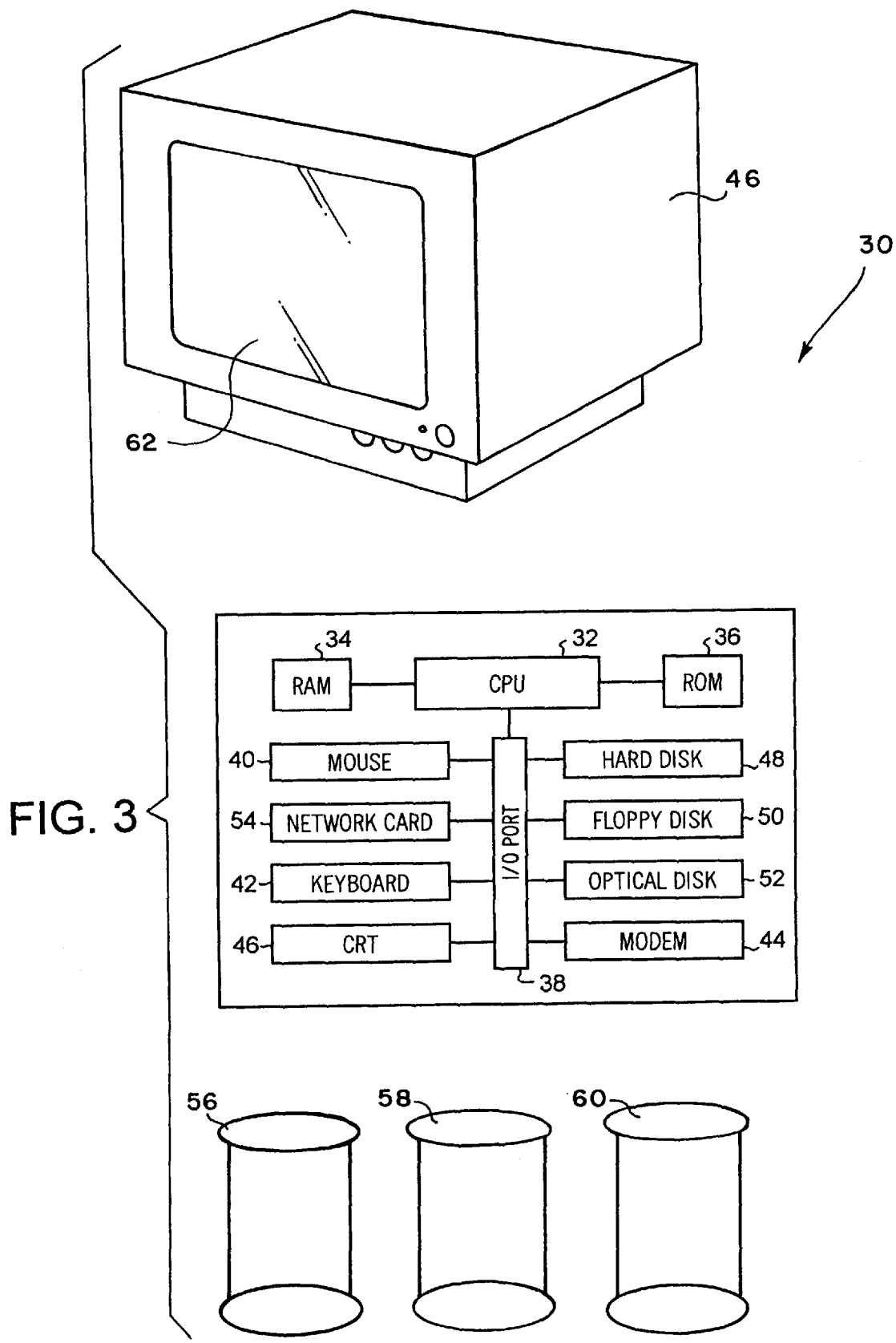
FIG. 3 is a schematic view of the control computer system of the present invention.

Referring now to FIG. 3, there is shown one embodiment of a control computer based system 30, of the present invention, for identifying nucleic acid sequences for antisense oligonucleotide targeting. The control computer 30 may be a personal computer which is composed of CPU 32, RAM 34, ROM 36 and Input/Output ports 38. Various peripheral units may be connected to I/O ports 38 such as mouse 40, keyboard 42 and modem 44. A CRT 46 may be used to display information generated by control computer 30. Control computer 30 may also include hard disk 48, floppy disk 50, and optical disk 52. Control computer 30 may be connected to a computer network via network card 54 or modem 44.

The NNTSA program 56 of the present invention is operated by control computer 30 and may be stored in memory on hard drive 48, floppy disk 50 or optical disk 52. A nucleic acid nearest-neighbor combination pair value data list 58 may be accessed by control computer 30 while control computer 30 is operating NNTSA program 56. The nucleic acid nearest neighbor combination pair value data list 58 may be stored in the memory of control computer 30 on hard drive 48, floppy disk 50 or optical disk 52 or may be remotely accessed via modem 44 or network card 54. The nucleic acid nearest-neighbor combination pair value data list 58 includes the values assigned to thirteen (13) combinations of the sixteen possible nearest-neighbor pairs, which provide for hybridization strength values based on Tm or $\Delta G°$ values and the nearest-neighbor effect, as described hereinbelow in Table 7 for S-DNA:RNA phosphorothioate backbone nucleic acid hybrids. The nucleic acid sequence 60 which is to be analyzed by the NNTSA program 56 may be input into control computer 30 via keyboard 42 or may be remotely accessed via network card 54 or modem 44.

Figure 4:
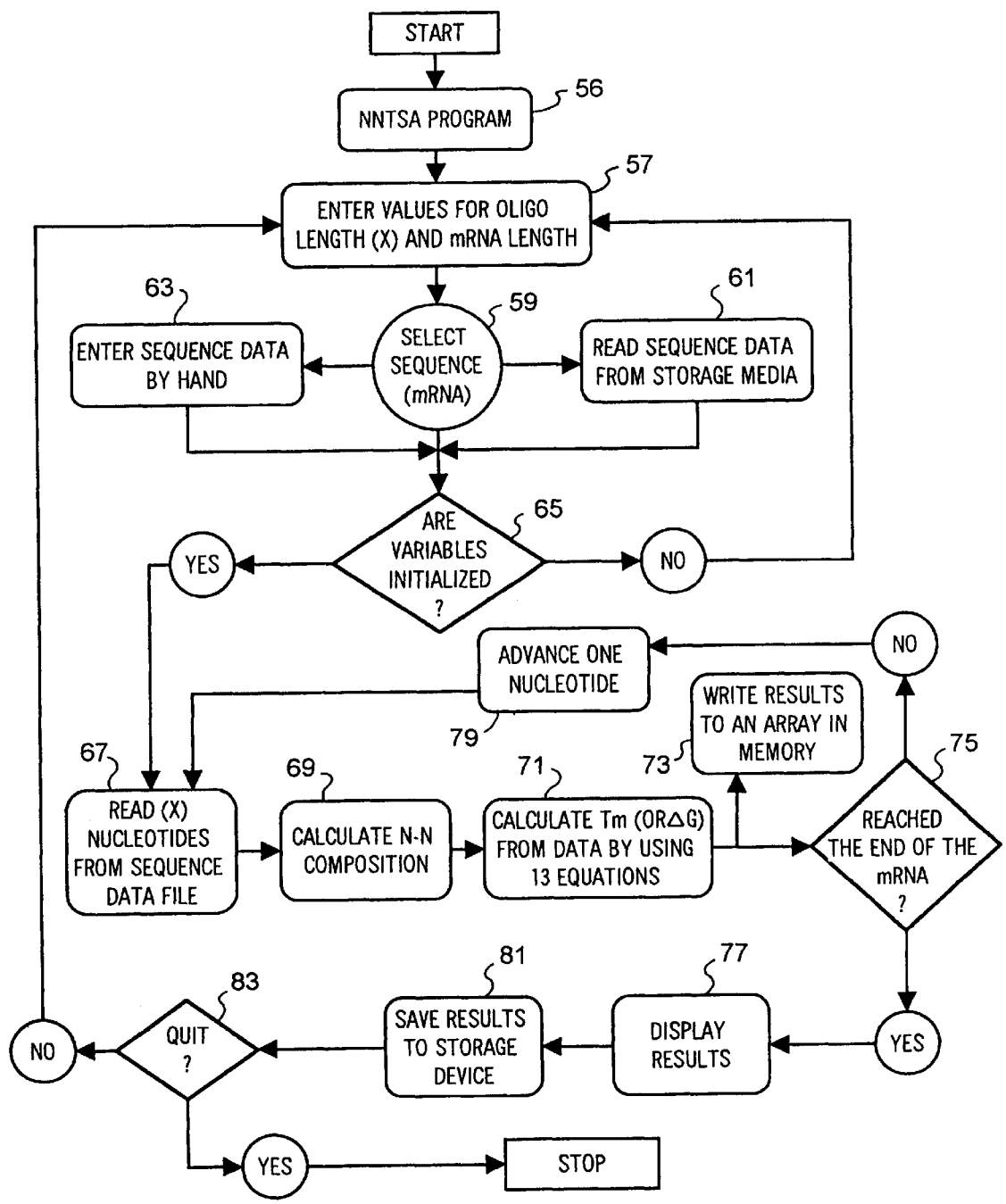
FIG. 4 represents the various ports of a logical flow diagram showing the overall operation of the present invention.

FIG. 4 is a flow diagram of the sequence of operation of the NNTSA program 56. In step 57, the NNTSA program 56 prompts the user to enter parameters for both the length of the oligonucleotide (default is 24) and the length of the messenger RNA (mRNA) to scan. The length of the mRNA to scan can range from a minimum length equal to that of the oligonucleotide to a maximum length equal to the total length of the mRNA. After both of these parameters have been entered, the NNTSA program 56 may proceed to the next step 59 where the mRNA sequence on which to perform an analysis is selected. This sequence can either be read in from an external memory source in step 61 or entered by the user in a text window in step 63. The NNTSA program 56 then checks to see it the initial parameters for oligonucleotide length and mRNA length have been entered and are valid in step 65. If the result is true, the NNTSA program 56 proceeds to step 67. If the result is false, the NNTSA program returns to step 57.

In step 67, the NNTSA program 56 reads into memory X number of nucleotides of the mRNA sequence where X is equal to the number of nucleotides specified for the oligonucleotide length in step 57. In step 69, the NNTSA program 56 calculates the nearest-neighbor composition of the sequence of nucleotides just previously read. The result is a tally for each of the 16 possible nearest-neighbor base pairs ($nn_1$=A, $nn_2$=B, $nn_3$=C, etc.). The NNTSA program 56 then substitutes these values into the appropriate nearest-neighbor equations in combination with the nearest-neighbor pair value data list 58 to determine the relative stability (either Tm or $\Delta G°$ depending on the data set used) of the sequence in step 71. In step 73, the results of the calculation are stored in an array in memory with each successive result occupying a separate position in the array. In step 75, the NNTSA program 56 checks to see if the end of the mRNA sequence has been reached. If the result is true, the NNTSA program 56 proceeds to step 77. If the result is false the program proceeds to step 79.

If the end of the mRNA sequence has not been reached, the NNTSA program 56 increments one nucleotide further down the mRNA sequence, increments the position mark by one unit and returns to step 67. Once the end of the mRNA sequence has been reached, the results of all calculations are routed to an output device, such as CRT 46. In step 81, the user may save the results to a storage device such as hard disk 48 or floppy disk 50. In step 83 the user may select the quit button in which case the NNTSA program 56 is ended, otherwise the user is free to execute the program multiple times as necessary by returning to step 57.

As stated, the output from the analysis described in FIG. 4 may be viewed on screen 62 by scanning through the nucleic acid sequence, or may be viewed via a computer print-out. Other means of analyzing the values may be through further computer manipulations. These manipulation can include viewing the list of values based on nucleic acid content or by increasing or decreasing hybridization rank value, to name some examples. The hybridization rank values assigned to each segment may also be transferred to another dynamic or permanent storage medium before or after analysis.

Figure 5:
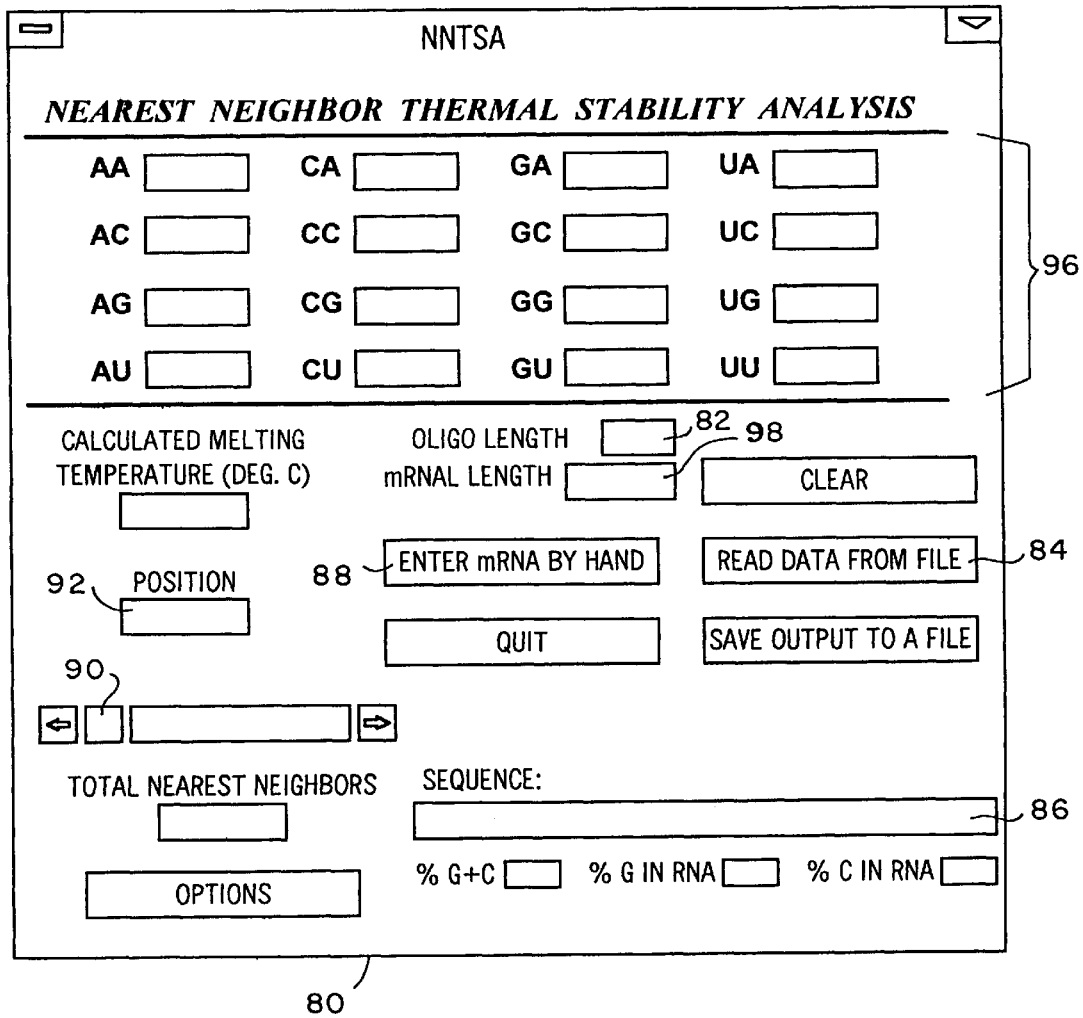
FIG. 5 illustrates a typical nearest-neighbor display screen generated by the system of the present invention.

FIG. 5 depicts a graphical user interface or screen 80 which may be used by the present invention to request information for a nucleic acid nearest-neighbor analysis. The screen 80 includes an oligo length user defined input window 82. Screen 80 also includes a READ DATA FROM FILE button 84, that permits the user to browse through, for example: a disk drive, hard drive or network, for a nucleic acid sequence. Once acquired and processed, the nucleic acid sequence appears in the sequence window 86. Alternatively, the nucleic acid sequence can be input by hand by pressing the Enter mRNA by Hand button 88. The nucleic acid sequence is then input by hand via a keyboard or any other input device. Using the scroll bar 90 the relative position of the nearest-neighbor segment analysis is displayed in the position window 92, which conforms with the sequence displayed in the sequence window after processing is complete. The individual count of each nearest-neighbor pair per oligo length segment is displayed in each of the nearest-neighbor pair boxes 96. Also available is the operator-specified length of the mRNA which is displayed in the mRNA length window 98. Another output available for display from the screen is the total number of nearest-neighbors that is in the segment length being displayed in the sequence window 86.

Practical Uses of the Apparatus

A DNA oligonucleotide of more than about 17 nucleotides in length would have a unique sequence relative to the entire human genome, as set forth in the article by Stein and Chen (1993). mRNAs are each much longer, 100's to 1000's of nucleotides long, and provide many overlapping target sites for binding of an antisense DNA oligomer (ASO). Table 1 below illustrates this fact for a short segment of a theoretical mRNA sequence to which many ASO's 10 nucleotides long (10-mers) may be targeted.

complexes or complexes with other cellular components that bind specific sequences). There are 16 DNA:RNA hybrid nearest-neighbor base pairs, which are shown in Table 2, that must be considered.

TABLE 2

16 nearest-neighbor base pairs in DNA:RNA hybrids
The RNA sequence is on the top and DNA is on the bottom. The strand directions are 5'-3' on the top and 3'-5' on the bottom.

| 1 | r(U-A) | 2 | r(U-U) | 3 | r(U-C) | 4 | r(U-G) |
|---|--------|---|--------|---|--------|---|--------|
|   | d(A-T) |   | d(A-A) |   | d(A-G) |   | d(A-C) |
| 5 | r(A-A) | 6 | r(A-U) | 7 | r(A-C) | 8 | r(A-G) |
|   | d(T-T) |   | d(T-A) |   | d(T-G) |   | d(T-C) |
| 9 | r(C-A) | 10 | r(C-U) | 11 | r(C-C) | 12 | r(C-G) |
|   | d(G-T) |   | d(G-A) |   | d(G-G) |   | d(G-C) |
| 13 | r(G-A) | 14 | r(G-U) | 15 | r(G-C) | 16 | r(G-G) |
|   | d(C-T) |   | d(C-A) |   | d(C-G) |   | d(C-C) |

There is a need to solve the problem of determining the relative contributions of each of these nearest-neighbor base pairs to the stability of a hybrid formed by an ASO sequence. Contributions of these individual nearest-neighbors generally cannot be separated as parts of complex nucleic acid sequences. They always appear in combinations whose properties can be determined. The apparatus and method of the present invention is based both on theory and experimental data: (a) for determining the minimum number of RNA:DNA sequence combinations whose properties need to

TABLE 1 mRNA:
    5'  —A—C—G—G—G—C—C—U—C—U—C—U—U—G—C—A—A—G—G—G—C—U—A—A—G—G—U—3' SEQ ID NO: 1

Possible overlapping 10-mer ASO's that could form base pairs with the mRNA starting at the 5' end of the mRNA:

3'  T—G—C—C—C—G—G—A—G—A  5' SEQ ID NO: 2
        G—C—C—C—G—G—A—G—A—G SEQ ID NO: 3
            C—C—C—G—G—A—G—A—G—A SEQ ID NO: 4
                C—C—G—G—A—G—A—G—A—A SEQ ID NO: 5
                    C—G—G—A—G—A—G—A—A—C SEQ ID NO: 6
                        G—G—A—G—A—G—A—A—C—G SEQ ID NO: 7
                            etc.

For a mRNA that is n nucleotides long, there are: n−m+1 different sequences (sites) to which m-mer ASO's can bind. One would like to know the relative stabilities of each possible ASO hybridized to its "target sequence zone" sequence and synthesize only those that will be most stable. Such optimization assures that only the most stable ones are tested as potential drugs, or as inhibitors of gene expression, thus creating a more expeditious and efficient process.

The thermodynamic stability of an ASO, i.e., the equilibrium constant that determines the proportion of ASO's of a given sequence that are bound to a target site, is a function of the structure of a given neighboring hybrid base pair, with the assumption that there are no intrastrand mRNA or intrastrand ASO complexes that compete with the binding in a sequence-specific manner. Any such considerations that might affect the availability or the concentration of the target sequence zone can be added as secondary considerations. The primary consideration is the relative merit of different sequence sites for binding ASO's where the mRNAs and ASO's are not involved in competing complexes (selfbe determined; and (b) for selecting the ASO sequence that will form the most stable hybrid among all those possible in a given target mRNA sequence, given that the mRNA target sequences are in equivalent states (i.e. not complexed, or identically complexed).

The nearest-neighbor base pairs are usually combined in a sequence. The only exceptions are the four sequences formed from homopolymers: r(U-U):d(A-A),r(A-A):d(T-T), r(C-C):d(G-G), r(G-G):d(C-C). Each of these four nearest-neighbors may exist as the sole type of nearest-neighbor in a sequence. Whenever more than one type of base is in each strand, there is a combination of nearest-neighbors. For example, the hybrid sequence $r(A-G)_{12}:d(C-T)_{12}$ has 12 nearest-neighbors of the type r(A-G):d(C-T) and 11 of the type r(G-A):d(T-C). All of the purines (A and G) are in the RNA strand and all of the pyrimidines C and T) are in the DNA strand:

```
                   1   2   3   4   5   6   7   8   9   10  11  12
SEQ ID NO: 8 mRNA: 5' A—G—A—G—A—G—A—G—A—G—A—G—A—G—A—G—A—G—A—G—A—G—A—G 3'

SEQ ID NO: 9 DNA:  3' T—C—T—C—T—C—T—C—T—C—T—C—T—C—T—C—T—C—T—C—T—C 5'
                       1   2   3   4   5   6   7   8   9   10  11
```

Also the above hybrid sequence is chemically different from the one below, which has the purines (A and G) in the DNA strand and the pyrimidines C and U) in the RNA strand:

```
                      1   2   3   4   5   6   7   8   9   10  11  12
mRNA SEQ ID NO: 10: 5' U—C—U—C—U—C—U—C—U—C—U—C—U—C—U—C—U—C—U—C—U—C 3'

DNA SEQ ID NO: 11:  3' A—G—A—G—A—G—A—G—A—G—A—G—A—G—A—G—A—G—A—G—A—G 5'
                        1   2   3   4   5   6   7   8   9   10  11
```

This oligomer duplex has 12 nearest-neighbors of the type r(U-C):d(G-A) and 11 of the type r(C-U):d(A-G). As shown in Table 3, the two oligomer duplexes diagramed above are of different stabilities. Table 3 gives the data for the melting temperatures (Tm values) of 16 oligomer duplexes, including oligomers containing alternating AG:CT (or AG:CU) basepairs. The DNA:DNA duplex has a Tm of 59.4 degrees. In comparison, the RNA:RNA duplex has a Tm of 69.5 degrees. These Tm values are different, and the Tm of a hybrid is not necessarily the average of these two values. The hybrid that has the purines bases A and G on the RNA strand has a Tm of 64.0 degrees while the hybrid that has the purine bases in the DNA strand is much less stable, with a Tm of 43.2 degrees. The same pattern holds for the other three sets of oligomer duplexes.

The hybrid duplexes are different in stability from duplexes of the DNA:DNA or RNA:RNA type, where both strands have the same sugar-phosphate backbone. In addition, the stability of hybrids cannot be determined by the simple (G+C)-content, since both of the hybrids in this example have 50% G:C base pairs and 50% A:T (or A:U) base pairs.

TABLE 3

Duplex Melting temperatures and Tm values
All sequences were 24 nucleotides long. The buffer was 0.05 M sodium phosphate, pH 7. Errors are ranges from 2–3 measurements (Hung et al. 1994).

|  | Tm (deg C.) |
|---|---|
| DNA:DNA Duplex | |
| d(AG):d(CT) | 59.4 ± 0.5 |
| d(AGG):d(CCT) | 63.4 ± 0.5 |
| d(AAG):d(CTT) | 50.0 ± 0.05 |
| d(AAGG):d(CCTT) | 57.9 ± 0.0 |
| RNA:RNA Duplex | |
| r(AG):r(CU) | 69.5 ± 1.0 |
| r(AGG):r(CCU) | 77.6 ± 0.3 |
| r(AAG):r(CUU) | 53.5 ± 1.5 |
| r(AAGG):r(CCUU) | 70.9 ± 0.0 |
| DNA:RNA Hybrid | |
| d(AG):r(CU) | 43.2 ± 0.8 |
| d(AGG):r(CUU) | 46.2 ± 0.8 |

TABLE 3-continued

Duplex Melting temperatures and Tm values
All sequences were 24 nucleotides long. The buffer was 0.05 M sodium phosphate, pH 7. Errors are ranges from 2–3 measurements (Hung et al. 1994).

|  | Tm (deg C.) |
|---|---|
| d(AAG):r(CUU) | 33.4 ± 1.4 |
| d(AAGG):r(CCUU) | 47.4 ± 0.5 |
| RNA:DNA Hybrid | |
| r(AG):d(CT) | 64.0 ± 0.9 |
| r(AGG):d(CCT) | 69.4 ± 0.5 |
| r(AAG):d(CTT) | 51.6 ± 1.2 |
| r(AAGG):d(CCTT) | 66.4 ± 0.5 |

Tm values for simple sequences (e.g. d(AA):r(UU) with one type of base pair repeated for at least 24 base pairs) can be estimated from the Tm values for more complex sequences, if one assumes that the Tm values are nearest-neighbor properties.

For example, the Tm for repeating d(AA):r(UU) can be derived from the Tm's for repeating d(AAG):r(CUU) (Tm of 33.4 deg C.) and for repeating d(AG):r(CU) (Tm of 43.2 deg C.). Since there are three types of nearest-neighbor base pairs in d(AAG):r(CUU) [namely, d(AA):r(UU), d(AG):r(CU), and d(GA):r(CU)] and two types of nearest-neighbor base pairs in d(AG):r(CU) [namely, d(AG):r(CU) and d(GA):r(UC)], one sets up the equation:

$$3 \times 33.4 \text{ deg C.} - 2 \times 43.2 \text{ deg C.} = 13.8 \text{ deg. C.}$$

This equation estimates the Tm for a sequence having only the d(AA):r(UU) nearest-neighbor pair, since the contributions of the other types of nearest-neighbor base pairs have been subtracted.

It may be recognized that sequence constraints on hybrid duplexes are the same as for single-stranded nucleic acids. The case is formally the same as published by Gray and Tinoco (1970), for single-stranded RNA's. The assumptions for deriving the sequence constraints are: (a) that the properties of nearest-neighbor base pairs dominate the properties of hybrid sequences, (b) that the conformations of nearest-neighbor base pairs are identical within all hybrid sequences and (c) that end effects are small. This appears to be true for polymers. The assumption results in only a 4% error for the 24-nucleotide long ASO's being discussed, and a proportionately lesser or greater error for sequences that are longer or shorter.

With these assumptions, there are three equations that constrain all hybrid duplex sequences. The equations state that the number of times a given base pair precedes another base pair must equal the number of times that it follows another base pair. (N(x) is the number of the nearest-neighbors of type x, where x is the numerical label of the nearest-neighbor base pair in Table 2.)

(1) N(1)+N(2)+N(3)+N(4) N(2)+N(6)+N(1)+N(14)
[i.e. number of times U:A appears first in a nearest-neighbor equals the number of time U:A appears second]
(2) N(S)+N(G)+N(7)+N(8) N(1)+N(5)+N(9)+N(13) [i.e. number of times A:T appears first in a nearest-neighbor equals the number of time A:T appears second]
(3) N(9)+N(10)+N(11)+N(12)=N(3)+N(7)+N(11)+N(15)
[i.e. number of times C:G appears first in a nearest-neighbor equals the number of time C:G appears second].

A similar equation may be written for the G:C base pair, but that equation may be derived as the sum of the above three equations. There are 16 nearest-neighbors minus 3 constraints=13 independent hybrid sequences whose properties, once known, can be used to predict the properties of all other hybrid sequences. Many sets of independent sequence combinations may be chosen. One of the simplest sets of hybrid polymer sequences is given in Table 4.

TABLE 4

An example set of 13 independent polymer DNA:RNA hybrid sequences 1. poly[r(U):d(A)]
2. poly[r(A):d(T)]
3. poly[r(G):d(C)]
4. poly[r(C):d(G)]
5. poly[r(AU):d(AT)]
6. poly[r(GU):d(AC)]
7. poly[r(CU):d(AG)]
8. poly[r(GA):d(TC)]
9. poly[r(CA):d(TG)]
10. poly[r(GC):d(GC)]
11. poly[r(GAU):d(ATC)]
12. poly[r(CAU):d(ATG)]
13. poly[r(CGU):d(ACG)]

The sequences could all have phosphorothioate DNAs, or DNAs modified in any other way, as long as all occurrences of a given nearest-neighbor base pair are similarly modified. For example, data have been obtained for hybrids where the antisense DNA oligomer contains phosphorothioate linkages, i.e. S-ASO's.

A complete set of 13 S-DNA:RNA hybrids was developed for use with the present invention, in which the DNA strand consists of phosphorothioate backbone linkages (S-DNA). The hybrids were formed with oligomers that were 24 nucleotides long in buffer conditions of 0.15M potassium (phosphate), pH 7.0. Melting profiles were obtained and the melting temperatures were determined. These data expand on the antisense technology in Table 3, because: (a) properties for other sequences, such as those in Table 4 may be derived from measured nearest-neighbor properties of these sequences; (b) the DNA strand has phosphorothioate linkages that render DNA oligomers more resistant to endogenous cellular nucleases, and (c) the buffer also includes a physiological cation concentration of 0.15M. The melting temperature data in Table 3 were obtained for oligomer hybrids containing normal phosphodiester linkages and were in 0.05M sodium phosphate, pH 7.0. The new Tm data were obtained for an entire set of 13 independent hybrid sequences. The results from these studies expand on the data presented hereinabove, and permit the use of the method and apparatus of the present invention for calculating the relative stabilities of hybrids formed with S-DNA antisense oligomers (S-ASO's).

The 13 hybrid sequences that have been studied and their melting temperatures are shown in Table 5. Note that the melting temperatures range from 44.1° to 66.6° C. and are significantly dependent on the sequence, for sequences having the same A+T or G+C composition. Thus, there is at least a nearest-neighbor dependence of the melting temperature.

TABLE 5

S-DNA:RNA Hybrids and their Tm values

| 13 Independent Sequences | Measured Tm (C.) | SD or Range | No. of Determination |
|---|---|---|---|
| 67% A+T | | | |
| 1 r(AGU)$_8$:S-d(ACT)$_8$ | 44.1 | 0.2 | 6 |
| 2 r(GAU)$_8$:S-d(ATC)$_8$ | 46.9 | 0.1 | 6 |
| 3 r(AAG)$_8$:S-d(CTT)$_8$ | 48.7 | 1.4 | 6 |
| 50% A+T | | | |
| 4 r(CCUU)$_6$:S-d(AAGG)$_6$ | 44.2 | 1.1 | 7 |
| 5 r(CU)$_{12}$:S-d(AG)$_{12}$ | 46.4 | 0.6 | 8 |
| 6 r(CGUU)$_{12}$:S-d(AACG)$_{12}$ | 46.5 | 0.4 | 6 |
| 7 r(GGUU)$_6$:S-d(AACC)$_6$ | 52.2 | 1.1 | 7 |
| 8 r(GU)$_{12}$:S-d(AC)$_{12}$ | 54.4 | 0.3 | 6 |
| 9 r(AG)$_{12}$:S-d(CT)$_{12}$ | 57.4 | 1.5 | 6 |
| 10 r(AC)$_{12}$:S-d(GT)$_{12}$ | 57.6 | 0.4 | 6 |
| 67% G+C | | | |
| 11 r(GCU)$_8$:S-d(AGC)$_8$ | 63.0 | 0.7 | 6 |
| 12 r(AGC)$_8$:S-d(GCT)$_8$ | 64.9 | 0.7 | 6 |
| 13 r(AGG)$_8$:S-d(CCT)$_8$ | 66.6 | 0.5 | 6 |

From the data of Table 5, the melting temperatures of any other independent hybrid polymer set, such as was selected for Table 4, can be derived using the nearest-neighbor formalism and the assumptions that end effects can be neglected and that differences in the entropy contributions for forming the different nearest-neighbor base pairs are small compared with the magnitude of the entropy ($\Delta S°$). Although this latter assumption is not strictly true, it is expedient for the present practical application.

The justification for these assumptions is shown in Table 6. The melting temperatures for three dependent sequences have been determined. Tm values of these sequences are compared with those calculated from the Tm values of the independent sequences in Table 13. The equations used to determine the values are shown as a footnote to Table 6. The average agreement between measured and calculated values is within 2° C. This difference is only slightly larger than the errors involved in the Tm measurements and is small compared with the total variation in Tm values of 22.6° C. for the independent sequences.

TABLE 6

Dependent S-DNA.RNA Hybrid Sequences and a test of the nearest-neighbor calculation of their Tm values

| Three Dependent Sequences | Measured Tm (C.) | Calculated Tm (C.) |
|---|---|---|
| 1  r(CUU)$_8$:S-d(AAG)$_8$ | 35.2 | 35.9* |
| 2  r(CGUU)$_6$:S-d(AAGC)$_6$ | 54.2 | 51.0** |
| 3  r(CGU)$_8$:S-d(ACG)$_8$ | 56.7 | 57.0*** |

In the calculations below, the numbers in ( ) indicate the number of the sequence in Table 13.
*Tm(r(CUU)$_8$:S-d(AAG)$_8$) = [4 Tm(7) + 2 Tm(5) + 2 Tm(9) − 3 Tm(13) − 2 Tm(8)]/3 Tm(r(CUU)$_6$:S-d(AAG)$_8$) = [4×52.4 + 2×46.1 + 2×57.4 − 3×66.6 − 2×54.6]/3 =0 35.9
**Tm(r(CGUU)$_6$:S-dAAGC)$_6$) = [4 × Tm(7) + 3 Tm(11) + 2 Tm(9) − 3 Tm(13) − 2 Tm(8)]/4 Tm(r(CGUU)$_6$:S-dAAGC)$_6$) = [4×52.4 + 3×63.0 + 2×57.4 − 3×66.6 − 2×54.4]/4 = 51.0
***Tm(r(CGU)$_6$:S-d(ACG)$_6$) = [4 × Tm(6) + 3 Tm(13) + 2 Tm(8) − 4 Tm(7) − 2 Tm(9)]/3 = [4 × 46.4 + 3 × 66.6 + 2 × 54.4 − 4 × 52.2 − 2X57.4]/3 = 57.0

Thus, the nearest-neighbor calculations can be used to obtain the Tm values for other dependent hybrid sequences. That is, the Tm values of the hybrid sequences in Table 5 can be combined to give the Tm values of any nearest-neighbor combinations in other dependent oligomer hybrid sequences that are at least 24 nucleotides long (i.e., polymers). The melting temperatures derived for the hybrid polymer sequences shown below in Table 7 are for the same sequences presented in the Table 4, but for which the DNAs have phosphorothioate linkages.

TABLE 7

The set of 13 independent polymer DNA:RNA hybrid sequences

Tm (C.) Derivation from data in Table 5
Numbers in () refer to polymers in Table 5

| | |
|---|---|
| 1. poly[r(U):S-d(A)] | 15.0 = 4 Tm(7) + 2 Tm(9) − 2 Tm(8) − 3 Tm(13) |
| 2. poly[r(A):S-d(T)] | 31.3 = 3 Tm(3) − 2 Tm(9) |
| 3. poly[r(G):S-d(C)] | 85.0 = 3 Tm(13) − 2 Tm(9) |
| 4. poly[r(C):S-d(G)] | 69.0 = 4 Tm(4) + 2 Tm(8) + 3 Tm(13) − 2 Tm(5) − 4 Tm(7) − 2 Tm(9) |
| 5. poly[r(AU):S-d(AT)] | 24.7 = [3 Tm(1) + Tm(2) − 2 Tm(8) − 2 Tm(9)[/2 |
| 6. poly[r(GU):S-d(AC)] | 54.4 = Tm(8) |
| 7. poly[r(CU):S-d(AG)] | 46.4 = Tm(5) |
| 8. poly[r(GA):S-d(TC)] | 57.4 = Tm(9) |
| 9. poly[r(CA):S-d(TG)] | 57.6 = Tm(10) |
| 10. poly[r(GC):S-d(GC)] | 79.2 = [4 Tm(6) + 3 Tm(11) + 3 Tm(13) − 2 Tm(5) − 4 Tm(7) − 2 Tm(9)]/2 |
| 11. poly[r(GAU):S-d(ATC)] | 46.9 = Tm(2) |
| 12. poly[r(CAU):S-d(ATG)] | 41.5 = [3 Tm(2) + 2 Tm(5) + 3 Tm(12) − 2 Tm(9) − 3 Tm(11)]/3 |
| 13. poly[r(CGU):S-d(ACG)] | 57.0 = [4 Tm(6) + 2 Tm(8) + 3 Tm(13) − 4 Tm(7) − 2 Tm(9)]/3 |

OPERATION

The procedure for finding the ASO (or S-ASO) sequence that will form the most stable hybrid is to find the one that would have the highest rank. The relative stabilities of the polymer sequences in Table 7 are assumed to be the same as the melting temperatures, derived as above. Other data to obtain a more accurate ranking of the 13 sequences with normal, with phosphorothioate, and with any other modified nucleotide linkages could be used. For example, the free energies of hybrid formation of these, or any other independent set of polymer sequences, can be obtained to rank the polymer stabilities to be used in the procedure. Different sets of polymers with different nucleotide linkages can also be used for the particular type of nucleotide linkages in the ASO's whose stabilities are to be calculated.

The procedure requires three steps. First, the fraction of each type of nearest-neighbor base pair in each target RNA:ASO-DNA hybrid sequence is determined. Second, the nearest-neighbor base pairs fractions are substituted in formulas already derived (Gray and Tinoco, 1970; and Table 8 below), in order to determine the fractions of each of the 13 polymers in Table 7 that, when summed, will have the same fractions of nearest-neighbors as in the RNA:ASO hybrid. Third, the fractions of the 13 polymers are multiplied by the stability rank (i.e. Tm values) from Table 7 and summed to give the rank of that ASO.

TABLE 8

Fractions of polymers needed to obtain the stability rank of an ASO.
The fractions are expressed as functions of the fractions of the
nearest-neighbor base pairs that would be in the hybrid formed by the
ASO. The numbering of the nearest-neighbors is as given in Table 2.
Equations are analogous to those derived by Gray and Tinoco (1970) for
single-stranded polymers, but where the ASO DNA strand is considered
to contain the single-strand nearest-neighbor fractions.

| Fractions of each polymer sequence | Fractions of the nearest neighbors formed by the ASO using the 5'-3' DNA strand orientation shown in Table 2 |
|---|---|
| F(1) = F(poly[r(U):d(A)]) | = f(dAA) = f(2); see Table 2 |
| F(2) = F(poly[r(A):d(T)]) | = f(dTT) = f(5) |
| F(3) = F(poly[r(G):d(C)]) | = f(dCC) = f(16) |
| F(4) = F(poly[r(C):d(G)]) | = f(dGG) = f(11) |
| F(5) = F(poly[r(AU):d(AT)]) | = 2 × f(dTA) = 2 × f(1) |
| F(6) = F(poly[r(GU):d(AC)]) | = 2 × f(dCA) − 2 × f(dTC) + 2 × f(dCT) |
|  | = 2 × f(4) − 2 × f(13) + 2 × f(8) |
| F(7) = F(poly[r(CU):d(AG)]) | = 2 × f(dAG) = 2 × f(10) |
| F(8) = F(poly[r(GA):d(TC)]) | = 2 × f(dCT) = 2 × f(8) |
| F(9) = F(poly[r(CA):d(TG)]) | = 2 × f(dGT) = 2 × f(7) |
| F(10) = F(poly[r(GC):d(GC)]) | = 2 × f(dGC) = 2 × f(15) |
| F(11) = F(poly[r(GAU):d(ATC)]) | = 3 × f(dTC) − 3 × f(dCT) |
|  | = 3 × f(13) − 3 × f(8) |
| F(12) = F(poly[r(CAU):d(ATG)]) | = 3 × f(dTG) − 3 × f(dGT) |
|  | = 3 × f(9) − 3 × f(7) |
| F(13) = F(poly[r(CGU):d(ACG)]) | = 3 × f(dCG) − 3 × f(dGC) |
|  | = 3 × f(12) − 3 × f(15) |

EXAMPLE 1

As an example, the rank of the ISIS #1939 S-ASO from the papers by Chiang, et al. (1991), and Stull, et al. (1992), can be used to calculate the hybrid rank in detail. The ranks of six 20 to 21-mers S-ASO's analyzed by Stull, et al., were used to compare the present method with that of Stull, et al., for determining the most stable ASO's.

Step (a): Write the DNA-ASO sequence in a 5'-to-3' orientation. The ISIS #1939 DNA (the numbering used by ISIS Pharmaceuticals) 20-mer ASO sequence from Table 9 below is:

5' C—C—C—C—A—C—C—A—C—T—T—C—C—C—C—T—C—T—C  3' SEQ ID NO: 12

16  16  16  16  4  14  16  4    14  8   5   13  16  16  16  8   13  8    13  16

The nearest-neighbor types are labeled with the numbers as shown in Table 2. The ISIS #1939 DNA sequence would cause these nearest-neighbor base pairs to be formed when the DNA hydrogen-bonds with an RNA target. Note that the DNA sequence is 5' to 3' and that the DNA nearest-neighbors in Table 2 are on the bottom, listed 3' to 5'. Also, the ends must be closed. This is necessary to assure that the final numbers of nearest-neighbors are the same in the rest of the sequence as in the sum of the polymer sequences. From these labeled numbers the fraction of each type of nearest-neighbor is calculated:

Fractions of each of the nearest-neighbors:

f(1) = 0
f(2) = 0
f(3) = 0
f(4) = 2/20
f(5) = 1/20

-continued

Fractions of each of the nearest-neighbors:

f(6) = 0
f(7) = 0
f(8) = 3/20
f(9) = 0
f(10) = 0
f(11) = 0
f(12) = 0
f(13) = 3/20
f(14) = 2/20

-continued

Fractions of each of the nearest-neighbors:

f(15) = 0
f(16) = 9/20

Total = 20/20

Step (b): Substitute the nearest-neighbor fractions in the formulas in Table 8 to obtain the fractions of each of the polymers. Note that not all of the 16 nearest-neighbor fractions need be involved in this step, because of the 3 constraints used to derive the 13 polymer sequences.

Fractions of each polymer sequence:

F(1) = F(poly[r(U):d(A)]) = f(2) =                           0
F(2) = F(poly[r(A):d(T)]) = f(5) =                          1/20

-continued

Fractions of each polymer sequence:

F(3) = F(poly[r(G):d(C)]) = f(16) =                                    9/20
F(4) = F(poly[r(C):d(G)]) = f(11) =                                    0
F(5) = F(poly[r(AU):d(AT)]) = 2 × f(1) =                               0
F(6) = F(poly[r(GU):d(AC)]) = 2 × f(4) − 2 × f(13) + 2 × f(8) =        4/20
F(7) = F(poly[r(CU):d(AG)]) = 2 × f(10) =                              0
F(8) = F(poly[r(GA):d(TC)]) = 2 × f(8) =                               6/20
F(9) = F(poly[r(CA):d(TG)]) = 2 × f(7) =                               0
F(10) = F(poly[r(GC):d(GC)]) = 2 × f(15) =                             0
F(11) = F(poly[r(GAU):d(ATC)]) = 3 × f(13) − 3 × f(8) =                0
F(12) = F(poly[r(CAU):d(ATG)]) = 3 × f(9) − 3 × f(7) =                 0
F(13) = F(poly[r(CGU):d(ACG)]) = 3 × f(12) − 3 × f(15) =               0

Total = 20/20

Step (c): Multiply the fractions obtained in step (b) by the polymer rankings in Table 7, and take the sum. This gives the "hybrid duplex stability rank (or Tm)" for the DNA:RNA hybrid formed with this ASO.

Hybrid duplex stability rank 1.  (poly[r(U):d(A)]) = F(1) * 15.0 = * 15.0 =              0
2.  (poly[r(A):d(T)]) = F(2) * 31.3 = (1/20) * 31.3 =       1.56
3.  (poly[r(G):d(C)]) = F(3) * 85.0 = (9/20) * 85.0 =       38.25
4.  (poly[r(C):d(G)]) = F(4) * 69.0 = * 69.0 =              0
5.  (poly[r(AU):d(AT)]) = F(5) * 24.7 = 0 * 24.7 =          0
6.  (poly[r(GU):d(AC)]) = F(6) * 54.4 = (4/20) * 54.4 =     10.88
7.  (poly[r(CU):d(AG)]) = F(7) * 46.4 = 0 * 46.4 =          0
8.  (poly[r(GA):d(TC)]) = F(8) * 57.4 = (6/20) * 57.4 =     17.22
9.  (poly[r(CA):d(TG)]) = F(9) * 57.6 = 0 * 57.6 =          0
10. (poly[r(GC):d(GC)]) = F(10) * 79.2 = 0 * 79.2 =         0
11. (poly[r(GAU):d(ATC)]) = F(11) * 46.9 = 0 * 46.9 =       0

-continued

Hybrid duplex stability rank 12. (poly[r(CAU):d(ATG)]) = F(12) * 41.5 = 0 * 41.5 =       0
13. (poly[r(CGU):d(ACG)]) = F(13) * 57.0 = 0 * 57.0 =       0

Total (hybrid duplex stability rank) =   67.91

The calculated stability rank of the ISIS #1939 sequence is 67.91 on a scale dictated by the polymer ranks in Table 7. This sequence forms a relatively stable DNA:RNA hybrid.

The advantage of the method of the present invention is that it discriminates between nearest-neighbor base pairs in polymers such as 7 and 8 in Tables 4 and 7. Other methods used for estimating hybrid stabilities have relied on data from either DNA:DNA or RNA:RNA duplexes Chiang, et al. (1991); and Stull, et al. (1992). In the cases of such duplexes where both strands have the same type of backbone, there are only 8 independent sequences in the nearest-neighbor approximation (Gray and Tinoco, 1970). Any method that relies on data obtained from DNA:DNA or RNA:RNA duplexes, where both strands are the same, essentially consider polymers such as 7 and 8 in Tables 4 and 7 to have identical stabilities since they are chemically identical when both strands are identical. Such methods will be valuable for predicting the stability of hybrids only if the hybrids under study do not have a significant difference in the numbers of the nearest-neighbors that are contained in such polymers.

Comparison with Stull et al.'s Dscore

One published report by Stull et al. (1992) has used a "Dscore", based on published thermodynamic stabilities of RNA:RNA duplex nearest-neighbors, to predict the inhibitory effects of S-ASO's in various experimental systems. Results, as they showed, should be in comparisons of S-ASO's of equal lengths. The most significant predictive indices were for a set of six 20 to 21-mer S-ASO's targeted against human "intracellular adhesion molecule-1" (ICAM-1) produced upon cytokine-induced expression in two cultured human cell lines (HUVEC—human umbilical vein endothelial cells, and A549—human lung carcinoma cells). Table 9 gives the six S-ASO sequences, the hybrid duplex stability scores of the present invention, Stull's Dscore, and the experimental inhibition in the two types of cells.

TABLE 9

| ISIS S-ASO sequence given 5' to 3' | Hybrid Rank | Stull's Dscore | inhibition HUVEC | A549 |
|---|---|---|---|---|
| ISIS #1934 T—G—C—C—C—A—T—C—A—G—G—G—C—A—G—T—T—T—G—A SEQ ID NO: 13 | 56.45 | −18.4 | 10 | 30 |
| ISIS #1938 C—C—T—G—T—C—C—C—G—G—G—A—T—A—G—G—T—T—C—A SEQ ID NO: 14 | 58.39 | −18.5 | 45 | 50 |
| ISIS #1939 C—C—C—C—C—A—C—C—A—C—T—T—C—C—C—C—T—C—T—C SEQ ID NO: 15 | 67.91 | −20.3 | 75 | 70 |
| ISIS #2302 G—C—C—C—A—A—G—C—T—G—G—C—A—T—C—C—G—T—C—A SEQ ID NO: 16 | 61.30 | −19.8 | 75 | 70 |
| ISIS #1572 G—A—C—A—C—T—C—A—A—T—A—A—A—T—A—G—C—T—G—G—T SEQ ID NO: 17 | 45.14 | −14.4 | 5 | 30 |
| ISIS #1940 T—T—G—A—G—A—A—A—G—C—T—T—T—A—T—T—A—A—C—T SEQ ID NO: 18 | 37.18 | −12.4 | 0 | 0 |

Table 10 gives the coefficients of correlation (r) for the revised stability ranks of the ISIS S-ASO sequence with the percent inhibition of the production of ICAM-1 in each type of cell culture as reported by Stull et al. (1992). Similarly, the (r) value is given for the absolute value of Stull's Dscore and compared to the percentage of inhibition. Correlation values range from +1 for perfect correlation to −1 for negative correlation. P is the significance of the correlation coefficient using the t-test. The smaller the value of P, the more significant the correlation. That is, the null hypothesis that there is no correlation, can be rejected.

TABLE 10

Correlation values, r, and test of significance

| Correlation of hybrid duplex stability rank with % Inhibition | | Correlation of Dscore with % Inhibition | |
|---|---|---|---|
| HUVEC Cells | A549 Cells | HUVEC Cells | A549 Cells |
| r = 0.878 | r = .931 | r = 0.839 | r = 0.908 |
| P < 0.02 | P < 0.01 | P < 0.05 | P < 0.02 |

As described above, and as presented in Table 10, the method of the present invention allows one to obtain a hybrid stability rank which is a better indicator than is the Dscore, for predicting the effectiveness of S-ASO sequences for inhibition of ICAM-1 expression within cells according to this limited set of data.

EXAMPLE 2
Explanation of data in U.S. Pat. No. 5,166,195 (Inventor D. J. Ecker)

U.S. Pat. No. 5,166,195 presents data relating to the use of oligomers to bind to the mRNA of the HIV tat protein, which trans-activates the transcription of a gene containing the "TAR" RNA element. The placental alkaline phosphatase gene (PAP) was used as a reporter gene, in a construct containing the TAR element, to assay the effectiveness of the oligomers to inhibit the production of the tat protein, and hence to inhibit the production of PAP (by preventing its trans-activation).

Six S-ASO sequences were used to inhibit PAP production, but there was no selection of which sequences should be the most effective. The method of the present invention provides such a selection and shows how the inhibition can be correlated with the sequence. Table 11 shows the sequences, the hybrid stability rank for each sequence, and the percent inhibition (average inhibition from data in FIG. 2 of the Ecker patent at 5–10 micromolar).

genome sequences can be attached by a third oligonucleotide strand to form a triplex sequence. The most common types of triplex sequences are illustrated in Table 12. The third strand of Triplex A is paired by Hoogsteen pairing to the purine strand of the usual Watson-Crick pair. The third strand of Triplex B is probably paired by reverse-Hoogsteen pairing to the purine strand of the Watson-Crick pair to form base triples (Pilch, et al., 1991; Laughton and Neidle, 1992). The illustrations are for DNA and well-known types of triplets, but the concepts may be readily extended to other triplexes with different base-pairing and to triplets having one or more non-DNA strands, or strands modified with different nucleotide linkages.

TABLE 12

Illustration of two types of DNA triplexes

Triplex A.
Third strand parallel to Watson-Crick purine strand. The base triples are C:G:C and T:A:T (The non-Watson-Crick third strand nucleotide is given first.) ("+" indicates that the cytosines in a third strand are protonated.)

| | |
|---|---|
| Third strand (Pyrimidines C and T): | 3'-------C+T--------5' |
| Watson-Crick Purine strand (G and A): | 3'-------GA----------5' |
| Watson-Crick Pyrimidine strand C and T): | 5'-------CT----------3' |

Triplex B.
Third strand anti-parallel to Watson-Crick purine strand.
Common base triples are G:G:C:, A:A:T, and T:A:T.

| | |
|---|---|
| Third strand (purines G,A, and pyrimidine T): | 5'-----AGT-------3' |
| Watson:Crick Purine strand (G and A): | 3'-----AGA-------5' |
| Watson:Crick Pyrimidine strand C and T): | 5'-----TCT-------3' |

It is recognized that the same theory of Gray and Tinoco (1970) can be used with the apparatus and method of the present invention to calculate the number of independent

TABLE 11

| S-ASO sequence in Pat No. 5,166,195 | Hybrid stability rank | % inhibition of PAP |
|---|---|---|
| #461<br>5' G—G—C—T—C—C—A—T—T—T—C—T—T—G—C—T—C—T—C—C 3' SEQ ID NO: 19 | 58.56 | 82 |
| #462<br>5' C—A—T—T—T—C—T—T—G—C—T—C—T—C—C—T—C—T—G—T 3' SEQ ID NO: 20 | 54.44 | 28 |
| #463<br>5' G—C—T—A—T—G—T—C—G—A—C—A—C—C—C—A—A—T—T—C 3' SEQ ID NO: 21 | 53.73 | 42 |
| #464<br>5' C—C—G—C—C—C—C—T—C—G—C—C—T—C—T—T—G—C—C—G 3' SEQ ID NO: 22 | 72.04 | 77 |
| #465<br>5' C—G—G—G—T—C—C—C—C—T—C—G—G—G—A—T—T—G—G—G 3' SEQ ID NO: 23 | 64.58 | 74 |
| #466<br>5' C—A—C—C—T—T—C—T—T—C—T—T—C—T—A—T—T—C—C—T 3' SEQ ID NO: 25 | 51.37 | 2 |

The stability rank has a correlation coefficient r=0.776 (P=0.07) with the percent inhibition values. By their stability ranks, sequences # 461, 464 and 465 would be predicted to be the most inhibitory, which they are.

Analyzing Triplex-Forming Sequences and Antigene Oligomers

The present invention can be readily extended to predict the most stable triplex-forming sequences, or antigene oligomers (AGOs). It is known that certain duplex DNA third strand sequences in such cases. The number of independent third strand sequences is restricted in exactly the same way as are single-strand sequences, because there is no symmetry in the overall triplex structure. For two types of triples (Triplex A in Table 12), there are 3 independent triplex sequences, and for three types of triples (Triplex B in Table 12), there are 7 independent sequences. Examples of sets of independent sequences are listed in Table 13 for these two types of triplexes.

TABLE 13

Example sets of independent triplex DNA:DNA:DNA
Example sets of independent triplex DNA:DNA:DNA sequences for the two types of triplexes illustrated in Table 12. The sequence in the third strand is given first for each triplex polymer sequence. Sequences are given for all three strands in the 5'-to-3' direction.

(A) Two type of base triples. Three (3) independent sequences are required.

| | Tentative stability rank |
|---|---|
| 1. poly[d(T):d(A):d(T)] | 3 (highest) |
| 2. poly[d(C+):d(G):d(C)] | 1 (lowest) |
| 3. poly[d(TC+):d(AG):d(CT)] | 2 |

(B) Three types of base triples. Seven independent sequences are required.

1. poly[d(A):d(A):d(T)]
2. poly[d(T):d(A):d(T)]
3. poly[d(G):d(G):d(C)]
4. poly[d(AT):d(AA):d(TT)]
5. poly[d(AG):d(GA):d(TC)]
6. poly[d(GT):d(AG):d(CT)]
7. poly[d(ATG):d(GAA):d(TTC)]

The stabilities of the three independent sequences of Table 11A are tentatively ranked on the basis of data at pH 7.4 by Kiessling et al., 1992. The method of analysis provides direction to obtaining the type of information that is both sufficient and necessary for determining the most stable triplex sequences. The analysis can be expanded to include other types of base pair mismatches at each position (i.e. third strand bases that do not form the base triples listed above).

The method used for ranking the independent hybrid is with the assumption that the end effects are relatively small. That is, melting temperatures, or thermodynamic properties, should be obtained for sequences that are approximately 20 base pairs (or base triples) long, so that the ends are 5% of the total sequence.

Analyzing Short Hybrid Sequences with End Effects

The expanded theory as shown below, proves that if end effects must be taken into account, the stabilities of hybrids (of varying length and with the four normal base pairs) must be obtained for 20 independent sequences. Therefore, the method described above in detail is based upon 13 polymer sequences (or long sequences) and is currently the most practical method for obtaining stabilities of hybrid sequences. But the method could be applied to a larger data set using shorter sequences should such data become available.

Same elements of a procedure for determining the number of independent sequences of short duplex sequences, with end effects, has been described by Goldstein and Benight, 1992. They did not apply the procedure to single-stranded sequences, and their procedure did not specify how to include sequences of varying length. The end (E) is treated like any other base (or base pair).

There will be 5×5=25 different nearest-neighbors whose properties we would like to obtain. Ends do not appear next to each other, which adds an additional constraint, but otherwise the constraint equations (the number of times one base comes before another must equal the number of times it comes after another base) are the same as for single-strands containing only the four usual bases.

TABLE 14

EQUATIONS

1. N(EE)=0 (a special equation for the ends)
2. N(AA)+N(AT)+N(AG)+N(AC)+N(AE)=N(AA)+N(TA)+N(GA)+N(CA)+N(EA)
3. N(TA)+N(TT)+N(TG)+N(TC)+N(TE)=N(AT)+N(TT)+N(GT)+N(CT)+N(ET)
4. N(GA)+N(GT)+N(GG)+N(GC)+N(GE)=N(AG)+N(TG)+N(GG)+N(CG)+N(EG)
5. N(CA)+N(CT)+N(CG)+N(CC)+N(CE)=N(AC)+N(TC)+N(GC)+N(CC)+N(EC)
6. N(EA)+N(ET)+N(EG)+N(EC)+N(EE)=N(AE)+N(TE)+N(GE)+N(CE)+N(EE)

Since equations 2+3-4-6=6, there are only 5 linearly independent equations. Therefore, the number of independent sequences of DNA:RNA hybrids that can vary in length is 25−5=20. As in the case of polymers of infinite length, it is not possible to determine the properties of all 25 individual nearest-neighbors (including the ends), but using the present invention one can obtain the properties of 20 independent sequences combinations from which the property of any other dependent sequence, of any length, can be obtained.

EXAMPLE 3

Example of application of the present method to obtain thermodynamic parameters

The following is an illustration that the procedure of the present invention for extracting information from thermodynamic measurements of oligomers as compared with recently published thermodynamic values for the 16 nearest-neighbor base pairs of DNA:RNA hybrid sequences (Sugimoto et al., 1995). The data in this publication are for nucleic acids having normal phosphodiester bonds, and for oligomers in 1M NaCl (which is non-physiological). However, this does not impact the analysis and principles described in this example.

Sugimoto et al. (1995) measured the thermodynamic values for 64 different DNA:RNA hybrid sequences, and performed a least-squares fit of these values to 16 hybrid base pair nearest-neighbors (Table 20, hereinbelow) plus one initiation parameter. Tabulated values from their Table 3 are listed below, but with the nearest-neighbors rearranged to be in the same order as in the present application:

TABLE 15

| Nearest-Neighbor Sequence* | $\Delta H°$ (kcal/mol) | $\Delta S°$ (cal/(mol °K.)) | $\Delta G°$ (37° C.) (kcal/mol) |
|---|---|---|---|
| rUA/dAT | −7.8 | −23.2 | −0.6 |
| rUU/dAA | −11.5 | −36.4 | −0.2 |
| rUC/dAG | −8.6 | −22.9 | −1.5 |
| rUG/dAC | −10.4 | −28.4 | −1.6 |
| rAA/dTT | −7.8 | −21.9 | −1.0 |
| rAU/dTA | −8.3 | −23.9 | −0.9 |
| rAC/dTG | −5.9 | −12.3 | −2.1 |
| rAG/dTC | −9.1 | −23.5 | −1.8 |
| rCA/dGT | −9.0 | −26.1 | −0.9 |
| rCU/dGA | −7.0 | −19.7 | −0.9 |
| rCC/dGG | −9.3 | −23.2 | −2.1 |
| rCG/dGC | −16.3 | −47.1 | −1.7 |
| rGA/dCT | −5.5 | −13.5 | −1.3 |
| rGU/dCA | −7.8 | −21.6 | −1.1 |
| rGC/dCG | −8.0 | −17.1 | −2.7 |
| rGG/dCC | −12.8 | −31.9 | −2.9 |
| Initiation | +1.9 | −3.9 | +3.1 |

(taken from Table 3 of Sugimoto, et al. (1995))
*Sequences in both strands written 5' to 3'

The main point is that there are 5 constraints on the 25 combinations of nearest-neighbors (the 16 listed in the above table plus 9 types of nearest-neighbor ends represented as base pairs next to ends, rUE/dAE, rAE/dTE, rCE/dGE, rGE/dCE, rEU/dEA, rEA/dET, rEC/dEG, rEG/dEC and rEE/dEE, where the "end" base pair is E/E). The five constraints are described in Table 14 and its discussion. This means that there are 20, but only 20 (25−5=20) combinations of nearest-neighbor properties can really be derived from measurements on oligomer sequences. Sugimoto, et al. (1995) make the usual assumption of combining the properties of all eight possible types of ends into one "initiation" parameter. Although they assign values to the 17 resulting parameters (16 nearest-neighbors plus one initiation parameter), these values do not represent a unique or optimal solution to the problem of obtaining a list of thermodynamic values that can then be used to predict thermodynamic values for other sequences, since there are 20 parameters needed to define all possible sequences.

Table 16 shows the independent sequence combinations whose thermodynamic values can be assigned from the data published by Sugimoto et al. (1995) for 64 oligomer sequences. Values are not assigned to individual nearest-neighbors, but only to combinations of nearest-neighbors. The set below explicitly identifies the different base pair-plus-end neighbors. The values below were derived using a singular value decomposition program (Press, et al., 1992) to do the least squares fit.

TABLE 16

Thermodynamic Values of 20 Nearest-Neighbor Combinations

| Nearest-Neighbor Combination* | ΔH° (kcal/mol) | ΔS° (cal/(mol °K.)) | ΔG° (37° C.) (kcal/mol) |
|---|---|---|---|
| rEUAE/dEATE | −12.9 | −48.4 | 2.1 |
| rEUUE/dEAAE | −8.3 | −34.5 | 2.4 |
| rEUCE/dEAGE | −12.7 | −45.8 | 1.5 |
| rEUGE/dEACE | −11.5 | −42.0 | 1.5 |
| rEAAE/dETTE | −11.7 | −44.7 | 2.1 |
| rEAUE/dETAE | −11.9 | −45.5 | 2.2 |
| rEACE/dETGE | −14.2 | −49.9 | 1.3 |
| rEAGE/dETCE | −13.1 | −47.1 | 1.5 |
| rECAE/dEGTE | −13.0 | −47.6 | 1.8 |
| rECUE/dEGAE | −8.2 | −32.4 | 1.8 |
| rECCE/dEGGE | −12.8 | −44.3 | 1.0 |
| rECGE/dEGCE | −17.8 | −61.1 | 1.2 |
| rEGAE/dECTE | −14.8 | −51.7 | 1.3 |
| rEGUE/dECAE | −13.7 | −49.3 | 1.6 |
| rEGCE/dECGE | −17.0 | −56.2 | 0.5 |
| rEGGE/dECCE | −16.5 | −54.6 | 0.5 |
| rEUE/dEAE | −3.0 | −18.3 | 2.7 |
| rEAE/dETE | −5.2 | −26.7 | 3.1 |
| rECE/dEGE | −6.9 | −31.9 | 3.0 |
| rEGE/dECE | −6.2 | −30.1 | 3.2 |

*Sequences in both strands written 5' to 3'

The thermodynamic values for specific nearest-neighbor base pairs cannot be determined (except for the homopairs rUU/dAA, rAA/dTT, rCC/dGG, and rGG/dCC). Nevertheless, the values for the 20 combinations in Table 16 can be combined to calculate the thermodynamic parameters for any other sequence. As an example, the ΔG° for the sequence r(EUGAAE)/d(EACTTE) is:

$$\Delta G° [r(EUGAAE)/d(EACTTE)] =$$
$$\Delta G° [EUGE/dEACE] + \Delta G° [EGAE/dECTE] + \Delta G° [EAAE/dETTE] -$$
$$\Delta G° [EGE/dECE] - \Delta G° [EAE/dETE] = -1.3 \text{ kcal/mol}$$

This equation is just the addition of the ΔG° values of all the nearest-neighbors in the sequence, minus those of the base pair-plus-ends for the interior base pairs, to balance the nearest-neighbors in the equation. Note that the resulting free energy is negative (i.e. favorable) for formation of this short duplex, even though the listed free energy values in Table 16 are positive.

Increased accuracy of the method of the present invention for obtaining thermodynamic parameters is described as follows. Using the values derived by Sugimoto et al. (1995) in Table 15 and the values in Table 16, the values of the 64 oligomers can be calculated and compared with the original, experimental values. Table 17 gives the standard deviations from the experimental values of those of those calculated from each set of derived values.

TABLE 17

Standard Deviations of Recalculated Thermodynamic Values for the Experimental Values of 64 Oligomers

| Calculation Method | ΔH° (kcal/mol) | ΔS° (cal/(mol °K.)) | ΔG° (37° C.) (kcal/mol) |
|---|---|---|---|
| Sugimoto, et al. | 5.8 | 19.1 | 0.45 |
| Table 16 | 4.3 | 13.5 | 0.31 |

All of the thermodynamic parameters are more accurately predicted using the methodology of the present invention. The method and apparatus of the present invention takes end effects into account, and do not require the extraction of explicit values for each nearest-neighbor base pair. The 64 sequences for which thermodynamic values were calculated ranged from 5 to 12 base pairs in length, with most being 8 base pairs in length. The decrease in error of about 0.14 kcal/mol reflects a difference of at least 0.28 kcal/mol for typical antisense sequences that are 16 or more base pairs in length.

The relation of percentage effectiveness of an antisense oligomer to the ΔG° is calculated as follows.

The equilibrium constant of

ASO+mRNA Target ⇌ ASO:mRNA hybrid is related to the free energy and is given by Keq=[ASO:mRNA hybrid]/([ASO][mRNA])=$e^{-\Delta G°/RT}$, where R is the gas constant (1.987 cal/(mol K)) and T is the absolute temperature. Taking the [ASO] concentration to be 100 nM and to be in excess over the target mRNA concentration (following the analysis of Freier et al., 1992), the ratio $$[ASO:mRNA \text{ hybrid}]/[mRNA]=[ASO]=e^{-\Delta G°/RT}=10^{-7}=e^{-\Delta G°/RT}.$$

This means that if one has an ASO sequence and conditions leading to a 50% hybridization at 37° C., the ΔG°=−RT ln(0.5×10$^{+7}$)=−9.5° kcal/mol. A difference of ±0.28 kcal/mol would result in hybridizations of:

$$[ASO:mRNA \text{ hybrid}]/[mRNA]=10^{-7} e^{+(9.5\pm0.28)/RT} = 0.32 \text{ to } 0.78$$
or 32% to 78%.

This example shows that, due to the exponential relation between the equilibrium constant and ΔG°, the application of the method of the present invention described herein is useful in calculating thermodynamic values for hybrid formation, leading to an improvement in the percentage of hybridization predicted by 18 to 28 percent (i.e. 50% versus 32 or 78%).

EXAMPLE 4

Correlation of Hybrid Stability Rank with Data for S-ASO's Against E-Selectin

Lesnik and Freier (1995) have published thermodynamic data on 28 oligonucleotide duplex DNA:RNA hybrids ranging from 8–21 base pairs in length having a DNA component which was not phosphorotioated. Their data were acquired in a buffer of 100 mMNa⁺, 10 mM phosphate, 0.1 mM EDTA, and a pH 7.1. The data indicated that under otherwise equal conditions, antisense oligonucleotides with 70–80% deoxypyrimidine content and moderate A:T/U content will be most effective at targeting structured mRNA. However, when testing this hypothesis against the biological activity for 33 antisense oligonucleotides, with phosphorothioated backbones, targeted to different regions of human E-selectin and VCAM-1 mRNAs, these authors concluded that no simple correlation between antisense activity and hybridization properties of DNA oligonucleotides to single-stranded RNA targets in solution existed because many other factors affect activity of antisense oligonucleotides. It should be noted that the genes encoding E-selectin and vascular cell adhesion molecule-1, or VCAM-1, are two of a group of genes that encode proteins that are induced on the luminal surface of vascular endothelium in response to inflammatory stimuli. Data were taken from Bennett et al., 1994.

However, the data presented by Bennett et al. (1994) for the inhibition by the nine antisense oligonucleotides directed to the 5'-untranslated region, AUG start codon, and coding regions of the E-selectin gene do show a significant correlation using the present method of ranking hybrid stabilities. These S-ASO's are listed in Table 18 below along with the calculation of the relative hybrid stabilities and the % inhibition of E-selectin.

TABLE 19

Correlation of % inhibition of E-selectin

| With Hybrid Duplex Stability Rank | With % Deoxypyrimidine | With % G + C |
|---|---|---|
| 0.851 | 0.615 | 0.766 |
| P = 0.004 | P = 0.08 | P = 0.02 |

The correlation % inhibition of E-selectin with the hybrid duplex stability rank is highly significant at P<0.01, certainly more significant than the correlations with the other simpler estimates of stability.

EXAMPLE 5

Prediction of Better S-ASO to Block Gag mRNA

HIV-1 retrovirus gene "Gag" encodes a glycoasminoglycan that functions as a virion core protein. The mRNA sequence is shown in Table 20 for the region surrounding the AUG start codon of Gag. Also shown in Table 20 is a 25-mer S-ASO that has been shown to inhibit HIV-1 replication (Lisziewicz et al., 1994). It has been designated as "GEM91", for Gene Expression Modulator 91. Using the methodology of the present invention, it has a hybrid stability rank of 59.9. A shift of just four nucleotides would give an S-ASO with a stability rank of 62.6 which is referred to as "GEM91-Optimal." From the correlations presented above for the predictive ability of the hybrid stability rank in

TABLE 18

| S-ASO sequence in Bennet et al. (1994) | Hybrid Stability Rank | % Inhibition of E-Selectin |
|---|---|---|
| #4764 (Target: 5'-untranslated region)<br>5' G—A—A—G—T—C—A—G—C—C—A—A—G—A—A—C—A—G—C—T 3' | 51.62 | 49.8 |
| #2687 (Target: 5'-untranslated region)<br>5' T—A—T—A—G—G—A—G—T—T—T—T—G—A—T—G—T—G—A—A 3'<br>SEQ ID NO: 27 | 40.86 | 26.2 |
| #2679 (Target: 5'-untranslated region)<br>5' C—T—G—C—T—G—C—C—T—C—T—G—T—C—T—C—A—G—G—T 3'<br>SEQ ID NO: 28 | 61.37 | 93.4 |
| #4759 (Target: 5'-untranslated region)<br>5' A—C—A—G—G—A—T—C—T—C—T—C—A—G—G—T—G—G—G—T 3'<br>SEQ ID NO: 29 | 54.80 | 79.8 |
| #2683 (Target: AUG codon)<br>5' A—A—T—C—A—T—G—A—C—T—T—C—A—A—G—A—G—T—T—C—T 3'<br>SEQ ID NO: 30 | 43.90 | 46.6 |
| #2686 (Target: AUG codon)<br>5' T—G—A—A—G—C—A—A—T—C—A—T—G—A—C—T—T—C—A—A—G 3'<br>SEQ ID NO: 31 | 45.81 | 48.6 |
| #4756 (Target: splice junction; coding region)<br>5' C—C—A—A—A—G—T—G—A—G—A—G—C—T—G—A—G—A—G—A 3'<br>SEQ ID NO: 32 | 49.89 | 64.3 |
| #4732 (Target: coding region)<br>5' C—T—G—A—T—T—C—A—A—G—G—C—T—T—T—G—G—C—A—G 3'<br>SEQ ID NO: 33 | 52.95 | 44.7 |
| #4730 (Target: splice junction; 3' region)<br>5' T—T—C—C—C—A—G—A—T—G—C—A—C—C—T—G—T—T—T 3'<br>SEQ ID NO: 34 | 55.87 | 97.7 |

The correlation coefficients between the % inhibition values and the calculated hybrid duplex stability ranks is given in Table 19. Also shown are the correlation coefficients between the % inhibition values and % deoxypyrimidine, and between the % inhibition values and % G+C contents, proposed by Lesnik and Freier (1995) to be a guide for selecting effective ASO's.

three other systems, there could be an increase of 2.9% inhibition/unit increase in hybrid stability rank. That is, GEM91-Optimal could show (62.2−59.9)×2.9=6.67% increase in inhibition of antiviral replication. The method of the present invention therefore reveals the possibility of such inhibition enhancement during the design of S-ASO sequences.

TABLE 20 mRNA: GACUAGCGGAGGCUAGAAGGAGAGAGAUGGGUGCGAGAGCGUCAGUAUUAAGCGGGGG SEQ ID NO: 35
S-ASO "GEM91":     TCTTCCTCTCTCTACCCACGCTCTC SEQ ID NO: 36
S-ASO "GEM91-Optimal": CCTCTCTCTACCCACGCTCTCGCAG SEQ ID NO: 37

EXAMPLE 6
Nearest-Neighbor Thermal Stability Apparatus and Method

The Nearest-Neighbor Thermal Stability Analysis apparatus and method (NNTSA v0.9) of the present invention processes data for use in calculating thermal melting temperatures for phosphorothioate DNA:RNA hybrids. The program relies on melting temperature data or $\Delta G°$ data for hybrids of phosphorothioate DNA 24-mers (24 nucleotides long) mixed with complementary RNAs of the same length in a 0.15M potassium buffer at physiologic pH (pH 7). Tm data predicted for other length hybrid duplexes are roughly estimated based on extrapolation of studies using 12-mers and 24-mers.

The distribution disk contains 12 files:
(1) Setup.ex_ (Part of installation program)
(2) Setup.1st (Part of installation program)
(3) NNTSA9.ex—(Compressed main program)
(4) DATA.in—(Compressed program data file)
(5) TEST.se—(Compressed sample input file)
(6) VBRUN300.dl—(Compressed program library)
(7) CMDIALOG.vb—(Compressed program library)
(8) GRID.vb—(Compressed program library)
(9) SETUP.ex—(Installation program)
(10) SETUPKIT.d1—(Compressed installation library)
(11) COMMDLG.d1—(Compressed program library)
(12) VER.dl—(Compressed installation library)

After installation, the target computer will contain the following files:
(1) NNTSA9.exe (Working program)
(2) DATA.ini (Program data file)
(3) TEST.seq (Sample program input file)
(4) VBRUN300.d11 (Program library, in windows system folder)
(5) CMDIALOG.vbx (Program library, in windows system folder)
(6) GRID.vbx (Program library, in windows system folder)
(7) COMMDLG.d11 (Program library, in windows system folder)

System requirements

A 386 or higher processor (486 recommended) based PC running Microsoft Windows 3.1 or later may be used having 4 MB of RAM and 2 MB free hard disk space. A math co-processor is not required. A 486DX2-66 can process a sequence of 2500 bases in about 2 minutes.

STEPWISE PROCEDURE FOR OPERATING NNTSA

Program installation

An operating system, such as windows is initiated. The present example uses the windows operating system as an example, but other operating systems may be used with the present invention. A distribution disk is inserted into the A: drive (or the equivalent floppy drive) and "RUN" is select from the FILE menu of the program manager. Type A:setup (or B:setup, etc.) is entered and a self-executing program determines the files necessary for installation. The program may prompt the user for a folder in which to install the program files (the default is NNTSA). The program files, including a test sequence, and all necessary libraries (libraries are installed in the windows system folder), will then be copied to the hard drive and uncompressed. A new program group will be added having the same name as the folder the program was installed in (default is NNTSA) and inside will be created with an icon representing the program.

Preparing to run NNTSA

Double click on the NNTSA program icon (located in the NNTSA folder in the program manager). The main NNTSA program will come up in a window. To perform an analysis enter the length of the antisense sequence to use for analysis (the default is 24 bases) in the field labeled "Oligo Length". Next, the length of the RNA sequence to be analyzed is entered. For example, this sequence can be less than the total length of the RNA, e.g., if the mRNA has 3000 bases, 100 may be entered to analyze only the first 100 bases. Any number greater than the length of the oligo and equal to or less than the total length of the RNA can be used. The user can then choose whether to use length dependent correction by selecting the appropriate button in the "Options" dialog box (this is accessed by clicking on the OPTIONS button at the bottom of the main program window). The program is now ready to read in data.

Reading data into NNTSA

The apparatus and method of the present invention allows the program to accept RNA sequences in text file format denoted as .SEQ (the exact format of the .SEQ file is noted below) or RNA sequences can be entered manually.

Reading .SEQ Files into NNTSA

To read a .SEQ file into NNTSA and perform an analysis, the user can click on the "Read Data From File" button. A dialog box will appear asking the user to select a file (even though this program can read any text file, the "Read Data From File" dialog box only shows file with the extension .SEQ). Open the file for analysis (the file "test.seq" has been provided to practice with) by double clicking the file name or by selecting the file name and choosing the "OK" button (the cancel button aborts the analysis and drops the user back to the main program window). Analysis of the selected file will now begin in the main program window.

Entering mRNA Data by Hand

Alternatively, data can be entered manually into NNTSA by clicking on the "Enter mRNA by Hand" button. The user will be presented with a dialog box including an area to enter the RNA sequence. Enter the RNA sequence to be analyzed 5' to 3' (text will automatically wrap to the next line when the end of a line is reached). Tick marks are provided above the text entry box to help keep track of the number of bases entered. When the sequence has been entered, select the "OK" button. Analysis of the hand-entered sequence will now begin in the main program window.

When entering data by hand, the user will have to make sure to enter at least the number of bases specified in the "mRNA Length" text box located in the main program window. Entering more bases than the program has been asked to analyze will not cause problems, but entering too few bases will cause an error.

Analyzing and Saving Results

After the analysis of the data is complete, several aspects of the main program window will change. The user will now be presented with a scroll bar under the POSITION text box (if the number of bases in the mRNA is greater than the length of the oligo). This scroll bar can be used to move up and down the mRNA sequence and view the results of the analysis. The number in the position text box indicates the beginning position on the mRNA of an oligomer of the length specified by the user previously. The sequence of the mRNA position can be read from the SEQUENCE text box in the main program window and is written 5' to 3'. The calculated melting temperature of the hybrid can also be read from the main program window.

The results of the analysis can be saved as a text file (delimited by commas) and used to create a plot of the results. To save the analysis results, click the "Save Output to a File" button in the main program window. The user will be presented with a standard "Save As" dialog box entitled "Save Output". Select an appropriate destination on the hard drive (or floppy drive), give the file a name in the standard 8.3 format and choose "OK". This saved output can be opened in any graphing program which can import comma delimited text (such as DeltaGraph, Excel or SigmaPlot).

EXAMPLE 7

Saving File Format Files

File format for .SEQ text files

To save an mRNA sequence the file must be in the proper format so it can be read in by NNTSA. This format is simply a text file but it must have the information arranged so the program (NNTSA) can read it properly. An example of a .SEQ file is shown below.

This is a sample .SEQ file:

CUGCAGAAAUAACUAGGUACUAAGCCCGUUUGUGAAAAGUGGCCAAACCCAUAAAUUUGGCAAUUA
CAAUAAAGAAGCUAAAAUUGUGGUCAAACUCACAAACAUUUUUAUUAUAUACAUUUUAGUAGCUGA
UGCUUAUAAAAGCAAUAUUUAAAUCGUAAACAACAAAUAAAAUAAAAUUUAAACGAUGUGAUUAAG
AGCCAAAGGUCCUCUAGAAAAAGGUAUUUAAGCAACGGAAUUCCUUUGUGUUAGUACUAUUUUAAC
GAAUAAUAAAAUCAGGUAUAGGUAACUAAAAA

The file can contain a header (or not) of any length followed by a colon (:) and then the sequence. The three most important aspects of the .SEQ file are the colon(:), the sequence, and the absence of any spaces, carriage returns, or end of line characters. The colon tells the program where to begin reading in sequence data. Anything before the colon is ignored in the analysis. The header information is there only to help the user keep track of sequence files. Header information is not required by the program. The sequence of the mRNA can be entered by hand or copied from nucleic acid databases and pasted into a word processor. Sequence data should be entered 5' to 3'. After entering the sequence it is important to make sure there are no end-of-line characters or spaces interrupting the sequence. This can be done easily using a word processor such as Microsoft Word, Wordperfect, and the like. After the data have been entered the file should be saved with an extension of .SEQ so the program (NNTSA) will recognize it in the "Read Data From File" dialog box.

Length-Dependence Correction

As described Cantor and Schimmel, 1980, for a homologous series of sequences (e.g., $A_nU_n$: $A_n$ $U_n$) the melting temperature increases with length. The relationship is generally:

$$1/Tm = A + B/N,$$

where N is the chain length and A and B are constants for a given set of experimental conditions. Tm data were acquired for $S\text{-}d(AC)_n\text{:}r(GU)_n$, where $N(1)=12$ and $N(2)$ 24, and substituted into the above equation;

$$1/Tm(1) = A + B/N(1),$$

and $$1/Tm(2) = A + B/N(2).$$

This gives:

$$1/Tm(1) - B/N(1) = 1/Tm(2) - B/N(2),$$

and $$B = [1/Tm(1) - 1/Tm(2)]/[1/N(1) - 1/N(2)] = 2.2 \times 10^{-4}/0.0417 = {}^*5.28 \times 10^{-3}.$$

Therefore, for any other length N(3), assuming that the relationship is identical for all sequences, $$[1/Tm(\text{Calc length N}) - 1/Tm(\text{Calc 24-mer})]/[1/N - 1/24] = B; \text{ and } Tm(\text{Calc length N}) = \{1/Tm(\text{Calc 24-mer}) + [1/N - 1/24]^* 5.28 \times 10^{-3}\}^{-1}.$$

Source Code for Nearest-Neighbor Thermal Stability Analysis

```
       Sub Command1_Click ()
       form4.Hide

End Sub

Sub Command1_Click ()
10     Form6.Hide

End Sub
15

Sub Command1_Click ()
       On Error GoTo ErrorTrap:
               form3.Hide form1.Label24.Visible = 1

       If (Val(form1.Text20.Text) - Val(form1.Text19.Text)) <= 0 Then
             form1.HScroll1.Max = 1 form1.HScroll1.Visible = 0

30         Else form1.HScroll1.Max  =  Val(form1.Text20.Text)  -
       Val(form1.Text19.Text) + 1
                 form1.HScroll1.Visible = 1 form1.Label24.Visible = 1
       form1.Label23.Visible = 0
          form1.Refresh
              End If
```

```
        datafile = "data.ini"
        Open datafile For Input As #1

Input #1, slope
        Input #1, tm1
10      Input #1, tm2
        Input #1, tm3
        Input #1, tm4
        Input #1, tm5
        Input #1, tm6
15      Input #1, tm7
        Input #1, tm8
        Input #1, tm9
        Input #1, tm10
        Input #1, tm11
20      Input #1, tm12
        Input #1, tm13

25      Close #1 tempname = "temp.in"
        Open tempname For Output As #1
        Print #1, ":"; Text1.Text
        Close #1

        Open tempname For Input As #1

40      headstart:

header = Input$(1, #1)
```

```
      If header <> ":" Then
      GoTo headstart:
      End If
 5 datastart = Seek(1)
10 mrnalength = Val(form1.Text20.Text)
15
      seekposition = datastart

Seek #1, seekposition

20    Do Until seekposition >= mrnalength - length + datastart + 1

25    i = 0

NN1 = ""
      ist = ""
      buffer = ""
      length = Val(form1.Text19.Text)

OLIGO(q) = Input$(length, #1)

      Seek #1, seekposition 40    getist:

ist = Input$(1, #1)
```

```
    If ist = "a" Then
    ist = "A"
    End If

5  If ist = "c" Then
    ist = "C"
    End If

If ist = "g" Then
10  ist = "G"
    End If

If ist = "u" Then
    ist = "U"
15  End If

If ist = "t" Then
    ist = "U"
    End If
20
    If ist = "T" Then
    ist = "U"
    End If

25

If ist <> "A" And ist <> "G" And ist <> "C" And ist <> "U" Then
30          GoTo getist:
      End If 35  NN1 = ist 40
      For i = 2 To length
```

```
     begin:

buffer = Input$(1, #1)

5   If buffer = "a" Then
     buffer = "A"
     End If

If buffer = "c" Then
10   buffer = "C"
     End If

If buffer = "g" Then
     buffer = "G"
15   End If

If buffer = "u" Then
     buffer = "U"
     End If
20
     If buffer = "t" Then
     buffer = "U"
     End If 25   If buffer = "T" Then
     buffer = "U"
     End If 30
     If ist <> "A" And ist <> "G" And ist <> "C" And ist <> "U" Then
               GoTo begin:

35
         End If

If ist = " " Then GoTo begin:
40
     If ist = Chr(13) Then GoTo begin:

If ist = Chr(10) Then GoTo begin:
```

```
      continue:

5    If buffer = "A" Then

If NN1 = "A" Then
              AAarray(q) = AAarray(q) + 1
10            End If If NN1 = "C" Then
              CAarray(q) = CAarray(q) + 1
              End If
15
          If NN1 = "G" Then
              GAarray(q) = GAarray(q) + 1
              End If 20        If NN1 = "U" Then
              UAarray(q) = UAarray(q) + 1
              End If NN1 = "A"
25    End If If buffer = "C" Then GCcontent(q) = GCcontent(q) + 1
30        Ccontent(q) = Ccontent(q) + 1

If NN1 = "A" Then
              ACarray(q) = ACarray(q) + 1
35            End If If NN1 = "C" Then
              CCarray(q) = CCarray(q) + 1
              End If
40
          If NN1 = "G" Then
              GCarray(q) = GCarray(q) + 1
              End If
```

```
            If NN1 = "U" Then
                UCarray(q) = UCarray(q) + 1
            End If 5          NN1 = "C"
        End If If buffer = "G" Then
10
            GCcontent(q) = GCcontent(q) + 1
            Gcontent(q) = Gcontent(q) + 1

15
            If NN1 = "A" Then
                AGarray(q) = AGarray(q) + 1
                End If
20
            If NN1 = "C" Then
                CGarray(q) = CGarray(q) + 1
                End If 25          If NN1 = "G" Then
                GGarray(q) = GGarray(q) + 1

End If

30          If NN1 = "U" Then
                UGarray(q) = UGarray(q) + 1
                End If NN1 = "G"
35      End If If buffer = "U" Then 40          If NN1 = "A" Then
                AUarray(q) = AUarray(q) + 1
                End If
```

89

```
            If NN1 = "C" Then
                CUarray(q) = CUarray(q) + 1
            End If 5          If NN1 = "G" Then
                GUarray(q) = GUarray(q) + 1
            End If If NN1 = "U" Then
10              UUarray(q) = UUarray(q) + 1
            End If

NN1 = "U"

15      End If

Next i

Rem ******* last NN pair (imaginary) ************
20

If ist = "A" Then

If buffer = "A" Then
25              AAarray(q) = AAarray(q) + 1
            End If If buffer = "C" Then
                CAarray(q) = CAarray(q) + 1
30          End If If buffer = "G" Then
                GAarray(q) = GAarray(q) + 1
            End If
35
            If buffer = "U" Then
                UAarray(q) = UAarray(q) + 1
            End If 40
        End If If ist = "C" Then
```

```
            GCcontent(q) = GCcontent(q) + 1
            Ccontent(q)  = Ccontent(q)  + 1

5         If buffer = "A" Then
                ACarray(q) = ACarray(q) + 1
            End If If buffer = "C" Then
 10             CCarray(q) = CCarray(q) + 1
            End If If buffer = "G" Then
                GCarray(q) = GCarray(q) + 1
 15         End If If buffer = "U" Then
                UCarray(q) = UCarray(q) + 1
            End If
 20

End If

25     If ist = "G" Then

GCcontent(q) = GCcontent(q) + 1
            Gcontent(q)  = Gcontent(q)  + 1
 30

If buffer = "A" Then
                AGarray(q) = AGarray(q) + 1
            End If 35         If buffer = "C" Then
                CGarray(q) = CGarray(q) + 1
            End If If buffer = "G" Then
 40             GGarray(q) = GGarray(q) + 1
            End If If buffer = "U" Then
```

91

```
                UGarray(q) = UGarray(q) + 1
            End If

5      End If

If ist = "U" Then

10          If buffer = "A" Then
                AUarray(q) = AUarray(q) + 1
            End If If buffer = "C" Then
15              CUarray(q) = CUarray(q) + 1
            End If If buffer = "G" Then
                GUarray(q) = GUarray(q) + 1
20          End If If buffer = "U" Then
                UUarray(q) = UUarray(q) + 1
            End If
25

End If
30 form1.Text1.Text  = AAarray(q)
        form1.Text2.Text  = ACarray(q)
35      form1.Text3.Text  = AGarray(q)
        form1.Text4.Text  = AUarray(q)
        form1.Text5.Text  = CAarray(q)
        form1.Text6.Text  = CCarray(q)
        form1.Text7.Text  = CGarray(q)
40      form1.Text8.Text  = CUarray(q)
        form1.Text9.Text  = GAarray(q)
        form1.Text10.Text = GCarray(q)
        form1.Text11.Text = GGarray(q)
```

```
        form1.Text12.Text = GUarray(q)
        form1.Text13.Text = UAarray(q)
        form1.Text14.Text = UCarray(q)
        form1.Text15.Text = UGarray(q)
 5      form1.Text16.Text = UUarray(q)

10

15

20      NNTOTarray(q) = (AAarray(q) + ACarray(q) + AGarray(q) + AUarray(q)
        + CCarray(q) + CAarray(q) + CGarray(q) + CUarray(q) + GGarray(q) +
        GAarray(q) + GCarray(q) + GUarray(q) + UUarray(q) + UAarray(q) +
        UCarray(q) + UGarray(q))

25      form1.Text18.Text = NNTOTarray(q)

F1 = (UUarray(q)) / NNTOTarray(q)
        F2 = (AAarray(q)) / NNTOTarray(q)
        F3 = (GGarray(q)) / NNTOTarray(q)
30      F4 = (CCarray(q)) / NNTOTarray(q)
        F5 = 2 * (UAarray(q) / NNTOTarray(q))
        F6 = 2 * (UGarray(q) / NNTOTarray(q)) - 2 * (GAarray(q) /
        NNTOTarray(q)) + 2 * (AGarray(q) / NNTOTarray(q))
        F7 = 2 * (CUarray(q)) / NNTOTarray(q)
35      F8 = 2 * (AGarray(q)) / NNTOTarray(q)
        F9 = 2 * (ACarray(q)) / NNTOTarray(q)
        F10 = 2 * (GCarray(q)) / NNTOTarray(q)
        F11 = 3 * (GAarray(q)) / NNTOTarray(q) - 3 * (AGarray(q)) /
        NNTOTarray(q)
40      F12 = 3 * (CAarray(q)) / NNTOTarray(q) - 3 * (ACarray(q)) /
        NNTOTarray(q)
        F13 = 3 * (CGarray(q)) / NNTOTarray(q) - 3 * (GCarray(q)) /
        NNTOTarray(q)
```

93

```
    form1.Text17.Text = ((tm1 * F1) + (tm2 * F2) + (tm3 * F3) + (tm4 *
    F4) + (tm5 * F5) + (tm6 * F6) + (tm7 * F7) + (tm8 * F8) + (tm9 * F9)
 5  + (tm10 * F10) + (tm11 * F11) + (tm12 * F12) + (tm13 * F13))

seekposition = seekposition + 1
    Seek #1, seekposition 10
    position(q) = Val(seekposition - datastart)

form1.Text21.Text = position(q)

15  Tm(q) = ((tm1 * F1) + (tm2 * F2) + (tm3 * F3) + (tm4 * F4) + (tm5 *
    F5) + (tm6 * F6) + (tm7 * F7) + (tm8 * F8) + (tm9 * F9) + (tm10 *
    F10) + (tm11 * F11) + (tm12 * F12) + (tm13 * F13))

If form8.Option1.Value = True Then TmEst1(q) = 1 / (slope * ((1 /
20  length) - 1 / 24) + (1 / (Tm(q) + 273.15))) Else TmEst1(q) = Tm(q)
    + 273.15

TmEst(q) = TmEst1(q) - 273.15
25

GCcontent(q) = (GCcontent(q) / length) * 100

Gcontent(q) = (Gcontent(q) / length) * 100
30
    Ccontent(q) = (Ccontent(q) / length) * 100 form1.Text23.Text = GCcontent(q)
35  form1.Text24.Text = Gcontent(q)
    form1.Text25.Text = Gcontent(q)

q = q + 1
40
    form1.HScroll1.Value = q
```

94

```
        Loop

Close #1 datastart = 0
        mrnalength = 0
        seekposition = 0 form1.Label24.Visible = 0
        If (Val(form1.Text20.Text) - Val(form1.Text19.Text)) = 0 Then
            form1.HScroll1.Visible = 0
            form1.Text22.Text = OLIGO(0)
            form1.Text17.Text = TmEst(0)
            form1.Text23.Text = GCcontent(0)
            form1.Text24.Text = Gcontent(0)
            form1.Text25.Text = Ccontent(0)

End If form1.Text22.Visible = 1
        form1.Label25.Visible = 1
        form1.Text23.Visible = 1
        form1.Label26.Visible = 1
        form1.Text24.Visible = 1
        form1.Label27.Visible = 1
        form1.Text25.Visible = 1
        form1.Label28.Visible = 1
        form8.Option1.Visible = 1
        form8.Option2.Visible = 1
```

```
        form1.Refresh ending:

       Exit Sub

ErrorTrap:

On Error GoTo 0
10
           Close #1
           form1.HScroll1.Visible = 0
           form1.Label24.Visible = 0

15      form6.Show

Resume ending:

20      End Sub

Sub Command2_Click ()

Text1.Text = ""
25
        form3.Hide

End Sub

        Sub Analyze_Click ()
        AA = Val(Text1.Text)
        AC = Val(Text2.Text)
        AG = Val(Text3.Text)
        AU = Val(Text4.Text)
        CA = Val(Text5.Text)
        CC = Val(Text6.Text)
        CG = Val(Text7.Text)
        CU = Val(Text8.Text)
        GA = Val(Text9.Text)
        GC = Val(Text10.Text)
        GG = Val(Text11.Text)
        GU = Val(Text12.Text)
        UA = Val(Text13.Text)
```

```
        UC = Val(Text14.Text)
        UG = Val(Text15.Text)
        UU = Val(Text16.Text)

        text17 = AA + AC + AG
        End Sub

Sub Command1_Click ()
        Rem form5.Text1.Text = ""

Rem form5.Show
        On Error GoTo errorhandeler:

        CmDialog1.Action = 2 savename = CmDialog1.Filename

Open savename For Output As #1

Write #1, "position", "Tm", "GC content", "G content", "C content",
        "mRNA Target Sequence"

For H = 0 To q - 1

Write  #1,  position(H),  TmEst(H),  GCcontent(H),  Gcontent(H),
35      Ccontent(H), OLIGO(H)

Next H

40

Close #1
```

```
            q = 0
        i = 0 datastart = 0
   5    mrnalength = 0
        seekposition = 0 form2.Hide

10 errorhandeler:
        Exit Sub

15

End Sub

Sub Command2_Click ()
        getout = 0 command4.Visible = 1 form7.Show
         form7.Refresh form1.Label28.Visible = 0
        form1.Label25.Visible = 0
        form1.Text22.Visible = 0
        form1.Text23.Visible = 0
        form1.Label26.Visible = 0
        form1.Text24.Visible = 0
        form1.Label27.Visible = 0
        form1.Text25.Visible = 0
        form1.Label23.Visible = 1

Text1.Text = ""
        Text2.Text = ""
        Text3.Text = ""
        Text4.Text = ""
        Text5.Text = ""
```

```
        Text6.Text = ""
        Text7.Text = ""
        Text8.Text = ""
        Text9.Text = ""
        Text10.Text = ""
        Text11.Text = ""
        Text12.Text = ""
        Text13.Text = ""
        Text14.Text = ""
        Text15.Text = ""
        Text16.Text = ""
        text17.Text = ""
        text18.Text = ""
        TEXT21.Text = ""
        FORM3.Text1.Text = ""
        HSCROLL1.Visible = 0

        For i = 0 To 3999

NNTOTarray(i) = 0
        AAarray(i) = 0
        ACarray(i) = 0
        AGarray(i) = 0
        AUarray(i) = 0
        CCarray(i) = 0
        CGarray(i) = 0
        CUarray(i) = 0
        CAarray(i) = 0
        GGarray(i) = 0
        GAarray(i) = 0
        GCarray(i) = 0
        GUarray(i) = 0
        UUarray(i) = 0
        UAarray(i) = 0
        UCarray(i) = 0
        UGarray(i) = 0
        Tm(i) = 0
        TmEst(i) = 0
        TmEst1(i) = 0

GCcontent(i) = 0
```

```
        Gcontent(i) = 0
        Ccontent(i) = 0
      Next i
     length = 0 mrnalength = 0

10    seekposition = 0 datastart = 0 q = 0
15

Filename = ""
      savename = ""
20    tempname = ""

AA = 0
      AC = 0
25    AG = 0
      AU = 0
      CA = 0
      CC = 0
      CG = 0
30    CU = 0
      GG = 0
      GA = 0
      GU = 0
      GC = 0
35    UU = 0
      UC = 0
      UA = 0
      UG = 0

40    i = 0 f1 = 0
```

100

```
        f2 = 0
        f3 = 0
        f4 = 0
        f5 = 0
  5     f6 = 0
        f7 = 0
        f8 = 0
        f9 = 0
        f10 = 0
 10     f11 = 0
        f12 = 0
        f13 = 0

NNTOT = 0

        datastart = 0 mrnalangth = 0
        seekposition = 0
        q = 0
        H = 0 form7.Hide
 30

End Sub

       Sub Command3_Click ()
        If Val(text19.Text) > Val(text20.Text) Then
            form4.Show
            Exit Sub
          Else
 40

If text20.Text = "" Then
```

101

```
        form4.Show
          Exit Sub
        Else form2.Show
    form2.Refresh Call Command2_Click
    End If
      End If End Sub Sub Command4_Click ()

End

Unload Me

End Sub

Sub Command5_Click ()

FORM3.Text1.Text = ""

If Val(text19.Text) > Val(text20.Text) Then
        form4.Show
        Exit Sub
      Else If Val(text19.Text) = 0 Then
        form4.Show
        Exit Sub
      Else If text20.Text = "" Then
        form4.Show
```

102

```
        Exit Sub
      Else
     Call Command2_Click

FORM3.Show

End If
     End If
     End If

End Sub

Sub Command6_Click ()
getout = 1

Rem Call Command2_Click
command6.Visible = 0

End Sub

Sub Command7_Click ()
form8.Show

End Sub

Sub hscroll1_Change ()

TEXT21.Text = HSCROLL1.Value
X = HSCROLL1.Value - 1

If HSCROLL1.Max = 2 Then
    Text22.Text = OLIGO(X)
    form1.Text23.Text = GCcontent(X)
    form1.Text24.Text = Gcontent(X)
    form1.Text25.Text = Ccontent(X)
```

```
       Else text17.Text = TmEst(X)
       text18.Text = NNTOTarray(X)
       Text23.Text = GCcontent(X)
       form1.Text24.Text = Gcontent(X)
       form1.Text25.Text = Ccontent(X)

       form1.Text1.Text  = AAarray(X)
        form1.Text2.Text  = ACarray(X)
        form1.Text3.Text  = AGarray(X)
        form1.Text4.Text  = AUarray(X)
        form1.Text5.Text  = CAarray(X)
        form1.Text6.Text  = CCarray(X)
        form1.Text7.Text  = CGarray(X)
        form1.Text8.Text  = CUarray(X)
        form1.Text9.Text  = GAarray(X)
        form1.Text10.Text = GCarray(X)
        form1.Text11.Text = GGarray(X)
        form1.Text12.Text = GUarray(X)
        form1.Text13.Text = UAarray(X)
        form1.Text14.Text = UCarray(X)
        form1.Text15.Text = UGarray(X)
        form1.Text16.Text = UUarray(X)

Text22.Text = OLIGO(X)

End If
       End Sub

Sub HScroll1_Scroll ()
       hscroll1_Change
       End Sub

Sub Text1_Change    ()
 40
       End Sub

Sub Command1_Click ()

104
```

```
        On Error GoTo ErrorTrap:

form1.Command4.Visible = 0
        form1.Command6.Visible = 1
              form2.Hide If (Val(form1.Text20.Text) - Val(form1.Text19.Text)) <= 0 Then
            form1.HScroll1.Max = 1

10          form1.HScroll1.Visible = 0

Else 15                       form1.HScroll1.Max  =  Val(form1.Text20.Text)  -
        Val(form1.Text19.Text) + 1 form1.HScroll1.Visible = 1

20

End If 25
        length = Val(form1.Text19.Text)

form1.Label24.Visible = 1
        form1.Label23.Visible = 0 form1.Refresh

35 datafile = "data.ini"
40
        Open datafile For Input As #1

Input #1, slope
```

105

```
        Input #1, tm1
        Input #1, tm2
        Input #1, tm3
        Input #1, tm4
 5      Input #1, tm5
        Input #1, tm6
        Input #1, tm7
        Input #1, tm8
        Input #1, tm9
10      Input #1, tm10
        Input #1, tm11
        Input #1, tm12
        Input #1, tm13

15
        Close #1

20

25 start1:
30

If Right(file1.Path, 1) <> "\" Then
            opFileName = file1.Path & "\" & file1.FileName
            Else
            opFileName = file1.Path & file1.FileName
            End If mrnalength = 0

        seekposition = 0 datastart = 0
```

```
        q = 0

        Open opFileName For Input As #1

        headstart:

header = Input$(1, #1)

15

If header <> ":" Then
        GoTo headstart:
        End If
20 datastart = Seek(1) + 2

25 mrnalength = Val(form1.Text20.Text)

30      seekposition = datastart

Seek #1, seekposition

Do Until seekposition >= mrnalength - length + datastart + 1
35 i = 0
40
        NN1 = ""
        ist = ""
```

```
         buffer = ""

OLIGO(q) = Input$(length, #1)

        Seek #1, seekposition 10      getist:

ist = Input$(1, #1)

15      If ist = "a" Then
         ist = "A"
         End If

If ist = "c" Then
 20      ist = "C"
         End If

If ist = "g" Then
         ist = "G"
 25      End If

If ist = "u" Then
         ist = "U"
         End If
 30

If ist = "t" Then
         ist = "U"
         End If
 35
         If ist = "T" Then
         ist = "U"
         End If 40
         If ist <> "A" And ist <> "G" And ist <> "C" And ist <> "U" Then
                 GoTo getist:
```

108

```
        End If

5   NN1 = ist

10
     For i = 2 To length begin:
15
     buffer = Input$(1, #1)

If buffer = "a" Then
     buffer = "A"
20   End If

If buffer = "c" Then
     buffer = "C"
     End If
25
     If buffer = "g" Then
     buffer = "G"
     End If 30   If buffer = "u" Then
     buffer = "U"
     End If If buffer = "t" Then
35   buffer = "U"
     End If If buffer = "T" Then
     buffer = "U"
40   End If
```

```
        If ist <> "A" And ist <> "G" And ist <> "C" And ist <> "U" Then
                    GoTo begin:

5
            End If

If ist = " " Then GoTo begin:

10      If ist = Chr(13) Then GoTo begin:

If ist = Chr(10) Then GoTo begin:

15      continue:

20      If buffer = "A" Then

If NN1 = "A" Then
25              AAarray(q) = AAarray(q) + 1
                End If If NN1 = "C" Then
                CAarray(q) = CAarray(q) + 1
30              End If If NN1 = "G" Then
                GAarray(q) = GAarray(q) + 1
                End If
35
            If NN1 = "U" Then
                UAarray(q) = UAarray(q) + 1
                End If 40          NN1 = "A"
        End If If buffer = "C" Then
```

110

```
            GCcontent(q) = GCcontent(q) + 1
            Ccontent(q) = Ccontent(q) + 1

5          If NN1 = "A" Then
                ACarray(q) = ACarray(q) + 1
                End If If NN1 = "C" Then
10              CCarray(q) = CCarray(q) + 1
                End If If NN1 = "G" Then
                GCarray(q) = GCarray(q) + 1
15              End If If NN1 = "U" Then
                UCarray(q) = UCarray(q) + 1
                End If
20
            NN1 = "C"
         End If 25     If buffer = "G" Then GCcontent(q) = GCcontent(q) + 1
       Gcontent(q) = Gcontent(q) + 1

30          If NN1 = "A" Then
                AGarray(q) = AGarray(q) + 1
                End If If NN1 = "C" Then
35              CGarray(q) = CGarray(q) + 1
                End If If NN1 = "G" Then
                GGarray(q) = GGarray(q) + 1
40
                End If If NN1 = "U" Then
```

111

```
                UGarray(q) = UGarray(q) + 1
                End If

NN1 = "G"
 5      End If

If buffer = "U" Then

10          If NN1 = "A" Then
                AUarray(q) = AUarray(q) + 1
                End If If NN1 = "C" Then
15              CUarray(q) = CUarray(q) + 1
                End If If NN1 = "G" Then
                GUarray(q) = GUarray(q) + 1
20              End If If NN1 = "U" Then
                UUarray(q) = UUarray(q) + 1
                End If
25
            NN1 = "U"

End If

30  Next i

Rem ******* last NN pair (imaginary) ************

35  If ist = "A" Then

If buffer = "A" Then
40          AAarray(q) = AAarray(q) + 1
            End If

If buffer = "C" Then
```

112

```
              CAarray(q) = CAarray(q) + 1
           End If

If buffer = "G" Then
 5         GAarray(q) = GAarray(q) + 1
           End If

If buffer = "U" Then
           UAarray(q) = UAarray(q) + 1
10         End If

End If

15   If ist = "C" Then

GCcontent(q) = GCcontent(q) + 1
        Ccontent(q) = Ccontent(q) + 1

20      If buffer = "A" Then
           ACarray(q) = ACarray(q) + 1
           End If If buffer = "C" Then
25         CCarray(q) = CCarray(q) + 1
           End If If buffer = "G" Then
           GCarray(q) = GCarray(q) + 1
30         End If If buffer = "U" Then
           UCarray(q) = UCarray(q) + 1
           End If
35

End If

40   If ist = "G" Then

GCcontent(q) = GCcontent(q) + 1
     Gcontent(q) = Gcontent(q) + 1
```

113

```
        If buffer = "A" Then
            AGarray(q) = AGarray(q) + 1
        End If If buffer = "C" Then
            CGarray(q) = CGarray(q) + 1
        End If If buffer = "G" Then
            GGarray(q) = GGarray(q) + 1
        End If If buffer = "U" Then
            UGarray(q) = UGarray(q) + 1
        End If End If If ist = "U" Then If buffer = "A" Then
            AUarray(q) = AUarray(q) + 1
        End If If buffer = "C" Then
            CUarray(q) = CUarray(q) + 1
        End If If buffer = "G" Then
            GUarray(q) = GUarray(q) + 1
        End If If buffer = "U" Then
            UUarray(q) = UUarray(q) + 1
        End If End If
```

114

```
        form1.Text1.Text  = AAarray(q)
        form1.Text2.Text  = ACarray(q)
 5      form1.Text3.Text  = AGarray(q)
        form1.Text4.Text  = AUarray(q)
        form1.Text5.Text  = CAarray(q)
        form1.Text6.Text  = CCarray(q)
        form1.Text7.Text  = CGarray(q)
10      form1.Text8.Text  = CUarray(q)
        form1.Text9.Text  = GAarray(q)
        form1.Text10.Text = GCarray(q)
        form1.Text11.Text = GGarray(q)
        form1.Text12.Text = GUarray(q)
15      form1.Text13.Text = UAarray(q)
        form1.Text14.Text = UCarray(q)
        form1.Text15.Text = UGarray(q)
        form1.Text16.Text = UUarray(q)

NNTOTarray(q) = (AAarray(q) + ACarray(q) + AGarray(q) + AUarray(q)
        + CCarray(q) + CAarray(q) + CGarray(q) + CUarray(q) + GGarray(q) +
35      GAarray(q) + GCarray(q) + GUarray(q) + UUarray(q) + UAarray(q) +
        UCarray(q) + UGarray(q))

form1.Text18.Text = NNTOTarray(q)

40      F1 = (UUarray(q)) / NNTOTarray(q)
        F2 = (AAarray(q)) / NNTOTarray(q)
        F3 = (GGarray(q)) / NNTOTarray(q)
        F4 = (CCarray(q)) / NNTOTarray(q)
```

```
F5 = 2 * (UAarray(q) / NNTOTarray(q))
F6 = 2 * (UGarray(q) / NNTOTarray(q)) - 2 * (GAarray(q) /
NNTOTarray(q)) + 2 * (AGarray(q) / NNTOTarray(q))
F7 = 2 * (CUarray(q)) / NNTOTarray(q)
F8 = 2 * (AGarray(q)) / NNTOTarray(q)
F9 = 2 * (ACarray(q)) / NNTOTarray(q)
F10 = 2 * (GCarray(q)) / NNTOTarray(q)
F11 = 3 * (GAarray(q)) / NNTOTarray(q) - 3 * (AGarray(q)) /
NNTOTarray(q)
F12 = 3 * (CAarray(q)) / NNTOTarray(q) - 3 * (ACarray(q)) /
NNTOTarray(q)
F13 = 3 * (CGarray(q)) / NNTOTarray(q) - 3 * (GCarray(q)) /
NNTOTarray(q)

form1.Text17.Text = ((tm1 * F1) + (tm2 * F2) + (tm3 * F3) + (tm4 *
F4) + (tm5 * F5) + (tm6 * F6) + (tm7 * F7) + (tm8 * F8) + (tm9 * F9)
+ (tm10 * F10) + (tm11 * F11) + (tm12 * F12) + (tm13 * F13))

seekposition = seekposition + 1
    Seek #1, seekposition position(q) = Val(seekposition - datastart)

form1.Text21.Text = position(q)

Tm(q) = ((tm1 * F1) + (tm2 * F2) + (tm3 * F3) + (tm4 * F4) + (tm5 *
F5) + (tm6 * F6) + (tm7 * F7) + (tm8 * F8) + (tm9 * F9) + (tm10 *
F10) + (tm11 * F11) + (tm12 * F12) + (tm13 * F13))

If form8.Option1.Value = True Then TmEst1(q) = 1 / (slope * ((1 /
length) - 1 / 24) + (1 / (Tm(q) + 273.15))) Else TmEst1(q) = Tm(q)
+ 273.15

TmEst(q) = TmEst1(q) - 273.15

GCcontent(q) = (GCcontent(q) / length) * 100

Gcontent(q) = (Gcontent(q) / length) * 100

Ccontent(q) = (Ccontent(q) / length) * 100
```

```
        form1.Text23.Text = GCcontent(q)
        form1.Text24.Text = Gcontent(q)
        form1.Text25.Text = Gcontent(q)

5      q = q + 1 form1.HScroll1.Value = q

        DoEvents

If getout = 1 Then

GoTo loopout:
            End If

Loop
20 loopout:

25      Close #1

30      datastart = 0
        mrnalength = 0
        seekposition = 0

35
        form1.Label24.Visible = 0
        If (Val(form1.Text20.Text) - Val(form1.Text19.Text)) = 0 Then
            form1.HScroll1.Visible = 0
            form1.Text22.Text = OLIGO(0)
40          form1.Text17.Text = TmEst(0)
            form1.Text23.Text = GCcontent(0)
            form1.Text24.Text = Gcontent(0)
            form1.Text25.Text = Ccontent(0)
```

117

```
        End If form1.Text22.Visible = 1
   form1.Label25.Visible = 1
 5 form1.Text23.Visible = 1
   form1.Label26.Visible = 1
   form1.Text24.Visible = 1
   form1.Label27.Visible = 1
   form1.Text25.Visible = 1
   form1.Label28.Visible = 1
   form1.Label23.Visible = 1
   form1.Command6.Visible = 0
   form1.Command4.Visible = 1

   form1.Refresh ending:

20 Exit Sub

ErrorTrap:

On Error GoTo 0
25
      Close #1
     form1.HScroll1.Visible = 0
     form1.Label24.Visible = 0
     form6.Show
     form1.Command6.Visible = 0
     form1.Command4.Visible = 1
     form1.Refresh 35    Resume ending:

End Sub

Sub Command2_Click ()

form2.Hide
```

```
End Sub

Sub Dir1_Change ()

file1.Path = dir1.Path

End Sub

Sub Drive1_Change ()
start:
    On Error GoTo EH
dir1.Path = drive1.Drive
Exit Sub EH:
drive1 = "c:\"
On Error GoTo 0
Resume start:

End Sub

Sub File1_DblClick ()
Call Command1_Click

End Sub

Sub Form_Load ()

If Val(form1.Text19.Text) = Val(form1.Text20.Text) Then
    form1.HScroll1.Visible = 0
    Else
    form1.HScroll1.Visible = 1 form1.Refresh

End If

End Sub
```

119

```
Sub Command1_Click ()
form8.Hide

End Sub

Sub Command1_Click ()
 savename = Text1.Text

If savename = "abort" Then
GoTo ending:

End If

Open savename For Output As #1

Write #1, "position", "Tm", "GC content", "G content", "C content",
"OLIGO"

For H = 0 To q - 1

Write   #1,  position(H),  TmEst(H),  GCcontent(H),  Gcontent(H),
Ccontent(H), OLIGO(H)

Next H

Close #1
  q = 0
i = 0
```

```
        datastart = 0
        mrnalength = 0
        seekposition = 0

       form2.Hide ending:
10      form5.Hide

End Sub

15      Sub Command2_Click ()
        Text1.Text = "abort"

form5.Hide

20      End Sub

25
        Global   opFileName As String
        Global   savename As String
        Global   tempname As String
        Global   oligo(4000)
        Global   TmEst(4000)
        Global   TmEstl(4000)
        Global   slope
        Global   GCcontent(4000)
        Global   Gcontent(4000)
        Global   Ccontent(4000)

Global   getout

        Global   AA
        Global   AC
        Global   AG
```

```
        Global   AU
        Global   CC
        Global   CA
        Global   CG
        Global   CU
        Global   GG
        Global   GA
        Global   GC
        Global   GU
        Global   UU
        Global   UA
        Global   UC
        Global   UG
       Global   AAarray(4000)
        Global   ACarray(4000)
        Global   AGarray(4000)
        Global   AUarray(4000)
        Global   GAarray(4000)
        Global   GUarray(4000)
        Global   GCarray(4000)
        Global   GGarray(4000)
        Global   UUarray(4000)
        Global   UGarray(4000)
        Global   UCarray(4000)
        Global   UAarray(4000)
        Global   CAarray(4000)
        Global   CUarray(4000)
        Global   CGarray(4000)
        Global   CCarray(4000)

Global   NNTOTarray(4000)

        Global   f1
        Global   f2
        Global   f3
        Global   f4
        Global   f5
        Global   f6
        Global   f7
        Global   f8
```

The present invention may be carried out in other specific ways other than those set forth herein without parting from the spirit and essential characteristics and scope of the present invention. The present embodiments set forth above are to be considered in all respects as illustrative and non-restrictive and all changes coming within the equivalency range of the appended claims are intended to be embraced within this invention.

The present invention may be carried out in other specific ways other than those set forth herein without parting from the spirit and essential characteristics and scope of the present invention. The present embodiments set forth above are to be considered in all respects as illustrative and non-restrictive and all changes coming within the equivalency range of the appended claims are intended to be embraced within this invention.

REFERENCES

Agrawal, A., Goodchild, J., Civeira, M. P., Thornton, A. H., Sarin, P. S., and Zamecnik, P. Z., *Proc. Natl. Acad. Sci. U.S.A.* 85, 7079–7083 (1988).

Agrawal, S., Ikeuchi, T., Sun, D., Sarin, P. S., Konopka, A., and Maizel, J., *Proc. Natl. Acad. Sci. U.S.A.* 86, 7790 (1989).

Bennett, C. F., Condon, T. P., Grimm, S., Chan, H. and Chiang, M.-Y. "Inhibition of Endothelial Adhesion Molecule Expression with Antisense Oligonucleotides," *J. of Immunology,* 152, 3530–3540 (1994).

Buck, H. M., Koole, L. H., van Gendersen, M. H. P., Smith, L., Green, J. L., Jurriaans, S. and Goudsmit, J., *Science* 248, 208–212 (1990).

Cantor, C. R. and Schimmel, P. R., "Biophysical Chemistry Part III," Freeman, W. H., San Francisco, pp. 1187–1190 (1980).

Cavenave, C., Stein, C. A., Loreau, N., Thuong, N. T., Neckers, L. M., Subasinghe, C., Hélène, C., Cohen, J. S.,and Toulmé, J.-J., Nucl. Acids Res. 17, 4255–4273 (1989)

Chiang, M-Y, Chan, H., Zounes, M. A., Freier, S. M., Lima, W. F., and Bennet, C. F., "Antisense oligonucleotides Inhibit Intercellular Adhesion Molecule I Expression by Two Distinct Mechanisms," *J. Biol. Chem.* 266, 18162–18171, (1991).

Cohen, J. S. "Oligonucleotides - Antisense Inhibitors of Gene Expression," CRC Press, Boca Raton, Fla. (1989).

Corey, D. R. and Schultz, P. G., *Science* 238, 1401–1403, (1987) Ecker, D. J., U.S. Pat. No. 5,166,195 entitled "Antisense Inhibitors of the Human Immunodeficiency Virus Phosphorothioate Oligonucleotides."

Eckstein, F., *Anal. Biochem.* 54, 367–402, (1985).

Freier, S. M., Lima, W. F., Sanghvi, Y. S., Vickers, T., Zounes, M., Cook, P. D. & Ecker, D. J. (1992) Thermodynamics of Antisense Oligonucleotide Hybridization in "Gene Regulation: Biology of Antisense RNA and DNA" (Eds. Erickson, R. P. & Izant, J. G.) pp. 95–107, Raven Press, Ltd., New York.

Goodchild, J., Agrawal, S., Civeira, M. P., Sarin, P. S., Sun, D., and Zamecnik, P. C., *Proc. Natl. Acad. Sci. U.S.A.* 859, 5507–5511 (1988).

Gray, D. M., and Tinoco, Jr., L., "A New Approach to the Study of Sequence-Dependent Properties of Polynucleotides." *Biopolymers* 9, 223–244 (1970).

Hung, S. H., Qin, Y., Gray, D. M. and Ratliff, R. L., "Evidence from CD Spectra that d(purine), r(pyrimidine) and r(purine) and (pyrimidine) Hybrids are in Different Structural Classes," *Nucl. Acids Res.* 22, 4326–4334 (1994).

Laughton, D. A., and Neidle, S., "Prediction of the Structure of the Y+:R−:R+ Type DNA Triple Helix by Molecular Modeling," *Nucl. Acids Res.* 20, 6535–6541 (1992).

Lesnik, E. A, and Freier, S. M., "Relative Thermodynamic Stability of DNA, RNA, and DNA:RNA Hybrid Duplexes: Relationship with Base Composition and Structure," *Biochemistry* 35, 10807–10815 (1995).

Letsinger, R. L., Zhang, G. R., Sun, D. K., Ikeuchi, T., and Sarin, P. S., *Proc. Natl. Acad. Sci. U.S.A.* 84, 7706 (1987).

Letsinger, R. L., Zhang, G. R., Sun, D. K., Ikeuchi, T., and Sarin, P. S., *Proc. Natl. Acad. Sci. U.S.A.* 86, 6553 (1989).

Lisziewicz, J., Sun, D., Weichold, F. F., Thierry, A. R., Lusso, P., Tang, J., Gallo, R. L. and Agrawal, S., "Antisense Oligodeoxynucleotide Phosphorothioate Complementary to Gag mRNA Blocks Replication of Human Immunodeficiency Virus Type 1 in Human Peripheral Blood Cells," *Proc. Natl. Acad. Sci. U.S.A.,* 91, 7942–7946 (1994). Loose-Mitchell, D. S., TIBS, 9, 45–47 (1988).

Marcus-Sekura, C. J., *Anal. Biochem.,* 172, 289–295 (1988).

Matsukura, M., Shinozuka, K., Zon, G., Mitsuya, H., Reitz, M., Cohen, J. J. and Bruder, S., *Proc. Natl. Acad. Sci. U.S.A.* 84, 7706–7710 (1987);

Matsukura, M., Zoara, G., Shinozuka, K., Stein, C. A., Mitsuya, H., Cohen, J. S., Broder, S., *Gene* 72, 343–347 (1988)

Matteucci, M. D. and Wagner, R. W., "In Pursuit of Antisense," *Nature,* 384, 20–22 (1996).

Melton, D. A. (Ed.) "Antisense RNA and DNA," Cold Spring Harbor Press, Cold Spring Harbor (1988).

Mereola, D., and Cohen, J. S., *Cancer Gene Therapy* 2, 47–59 (1995).

Mori, K., Boiziau, C. and Cazenave, C., *Nucl. Acids Res.* 17, 8207 (1989).

Pilch, D. S., Levenson, C., and Shafer, R. H., "Structure, Stability, and Thermodynamics of a Short Intermolecular Purine-Purine-Pyrimidine Triple Helix," *Biochemistry* 30, 6081–6087 (1991).

Press, W. H., Teukolsky, S. A., Vetterling, W. T., and. Flannery, B. P., (1992) "Numerical Recipes in C, the Art of Scientific Computing," 2nd edition, pp. 59–70, Cambridge University Press, Cambridge, England.

Ratmeyer, L., Vinayak, R., Zhong, Y. Y., Zon, G., and Wilson, W. D., "Sequence specific thermodynamic and structural properties for DNA:RNA duplexes," Biochemistry 33, 5298–5304 (1994).

Sarin, P. S., Agrawal, S. M., Civeira, P., Goodchild, J., Ikeuchi, T. and Zamecnik, P. C., *Proc. Natl. Acad. Sci. U.S.A.* 85, 7448 (1988).

Shibahara, S., Mukai, S., Morisawa, H., Nakashima, H., Koboyashi, S., and Yamamoto, N., *Nucl. Acids Res.* 17, 239 (1989). Stein, C. A., and Chen, Y.-C., "Antisense Oligonucleotides as Therapeutic Agents—Is The Bullet Really Magical?" Science 261, 1004–1012 (1993).

Stein, C. A. and Cohen, J. S., *Cancer Research,* 48, 2659–2668 (1988).

Stein, C. A. and Cohen, J. S., "Oligodeoxynucleotides as Inhibitors of Gene Expression; a Review," *Cancer Research Vol.* 48. 2659–2668 (1988).

Stevenson, M., Iversen, P. L., *J. Gen. Virol.* 70, 2673 (1989).

Stull, R. A., Taylor, L. A., and Szoka, Jr., F. C., "Predicting Antisense Oligonucleotide Inhibitory Efficacy: A Computational Approach Using Histograms and Thermodynamic Indices," *Nucl. Acids Res.* 20, 3501–3508 (1992).

Sugimoto, N., Nakano, S., Katoh, M., Matsumura, A., Nakamuta, H., Ohmichi, T., Yoneyama, M., and Sasaki, M. (1995) Thermodynamic Parameters to Predict Stability of RNA/DNA Hybrid Duplexes, *Biochemistry* 34, 11211–11216.

Toulmé, J.-J. and Héléne, C., "Antimessenger oligodeoxynucleotides: an Alternative to Antisense RNA for Artificial Regulation of Gene Expression—A Review," Gene 72, 51–58 (1988).

Van der Krol, A. R., Mol, J. N., and Stuitje, A. R., BioTechniques, 6, 958–973 (1988).

Walder, J., *Genes & Development* 2, 502–504 (1988).

Walder, R. T. and Walder, J. A., *Proc. Natl. Acad. Sci. U.S.A.*, 85, 5011–5015 (1988).

Zaia, J. A., Rossi, J. J., Murakawa, G. J., Spallone, P. A., Stephens, D. A., Kaplan, B. E., Wallace, R. B. and Cantin, E. M., *J. Virol.* 62, 3914 (1988).

Zamecnik, P., Taguchi, C., Goodchild, J., and Sarin, P. S., *Proc. Natl. Acad. Sci. U.S.A.* 83, 4143–4146 (1986).

Zamenik, P. and Stephenson, M., *Proc. Natl. Acad Sci U.S.A.* 75, 280–284 (1978).

Zon, G., *Journal of Protein Chemistry*, 6, 131–145 (1987).

Zon, G., *Pharmaceutical Research*, 5, 539–549 (1988).

---

What is claimed is:

1. A method for selectively ranking nucleic acid molecules comprising antisense oligonucleotide for inhibitory efficiency comprising the steps of:

determining the fraction of each of a set of 13 nearest-neighbor nucleic acid base pair types in a target sequence zone RNA:ASO-DNA hybrid nucleic acid sequence;

substituting nearest-neighbor nucleic acid base pair fractions into formulas to determine the fractions of each of a series of 13 nearest-neighbor nucleic acid base pair types to provide determined fractions; and multiplying the fractions of the 13 nearest-neighbor nucleic acid base pair types by a stability ranking to the nucleic acid antisense sequence;

wherein the results are ordered to produce a ranking.

2. The method of claim 1, wherein for bases U and A, said nearest neighbor nucleic acid base pair types, N(x), are constrained by the formula $N(1)+N(2)+N(3)+N(4)=N(2)+N(6)+N(10)+N(12)$.

3. The method of claim 1 wherein, for bases C and G, said nearest neighbor nucleic acid and base pair types, N(x), are constrained by the formula $N(5)+N(6)+N(7)+N(8)=N(1)+N(5)+N(9)+N(13)$ where x is the numerical label of the nearest neighbor base pair in Table 2.

4. The method of claim 1, wherein said formula for a C:G pair is $N(9)+N(10)+N(11)+N(12)=N(3)+N(7)+N(11)+N(15)$.

5. The method of claim 1, wherein a hybrid duplex stability rank for the target sequence zone RNA:ASO-DNA hybrid nucleic acid sequence is determined by summing the totals of the determined fractions.

6. The method of claim 1, further comprising the step of comparing the rank to assess the relative stability of the target sequence zone RNA:ASO-DNA hybrid nucleic acid sequence.

7. A method for selectively ranking nucleic acid molecules comprising an antisense oligonucleotide for inhibitory efficiency comprising the steps of:

determining the fraction of nearest-neighbor base pair types in each of a set of nucleic acid target sequence zone RNA:ASO-DNA hybrid nucleic acid sequences;

substituting nearest-neighbor base pairs fractions into formulas to determine the fractions of a series of 13 nearest-neighbor nucleic acid base pair types and ranking said fractions that include the substituted nucleic acid sequences for stability to provide a stability ranking for each of the fractions;

multiplying the fractions of the 13 nearest-neighbor nucleic acid base pair types by the stability ranking to yield the rank of the antisense oligonucleotide;

wherein said rank of the antisense oligonucleotide corresponds to the inhibitory efficiency of said antisense oligonucleotide.

8. A method for selectively ranking an antisense sequence comprising the steps of:

determining the fraction of nearest-neighbor base triplet types in a set of nucleic acid sequences comprising a target sequence zone DNA:ASO-DNA triplex nucleic acid sequence;

substituting nearest-neighbor base pairs fractions into formulas to determine the fractions of each of the nearest-neighbor nucleic acid sequence triplet types and ranking said fractions that include the substituted nucleic acid sequence triplet types for stability to provide a stability ranking for each of the nearest-neighbor nucleic acid sequence triplet types; and multiplying the fractions of the nearest-neighbor triplet types by the stability ranking to yield the rank of the nucleic acid sequence antisense oligonucleotide;

wherein the results are ordered to produce a ranking.

9. The method of claim 8, wherein said step of substituting nearest-neighbor base pairs fractions into formulas comprises substitution in at least 7 nearest-neighbor base triplet types.

10. The method of claim 8, wherein a triplex stability rank for the target sequence zone DNA:ASO-DNA triplex formed is determined by substituting the totals of determined fractions.

11. The method of claim 8, further comprising the step of comparing the rank to assess the relative stability of the target sequence zone DNA:ASO-DNA triplex.

12. A method for ranking a nucleic acid antisense sequence for hybridization efficacy comprising the steps of:

determining the fraction of each type of in a set of nucleic acid sequences comprising a target sequence zone DNA:ASO-DNA triplex sequence;

substituting nearest-neighbor base pairs fractions into formulas to determine the fractions of each of the 13 nearest-neighbor base nucleic acid sequence triplex types;

multiplying the fractions of the 13 nearest-neighbor base triplex by the stability ranking to yield the rank of the nucleic acid sequence antisense oligonucleotide; and ranking antisense oligonucleotides according to maximum hybridization efficacy.

13. The method of claim 12, said step of substituting nearest-neighbor nucleic acid base pairs fractions into formula comprises substitution in at least 7 nearest-neighbor base triplet types.

14. The method of claim 12, further comprising the step of comparing the rank to assess a triplex target sequence zone DNA:ASO-DNA triplex stability rank.

15. The method of claim 12, further comprising the step of comparing the rank to assess the relative stability of the target sequence zone DNA:ASO-DNA triplex.

* * * * *

UNITED STATES PATENT AND TRADEMARK OFFICE
CERTIFICATE OF CORRECTION

PATENT NO : 5,856,103
DATED : January 5, 1999
INVENTOR(S) : DONALD M. GRAY

It is certified that error appears in the above-identified patent and that said Letters Patent is hereby corrected as shown below:

Claim 1, Col 131, line 21, delete "oligonucleotide" with --oligonucleotides--;

Claim 1, Col 131, line 32, after 'stability ranking to', insert --yield the rank of--;

Claim 2, Col 131, line 38, delete "N(12)" and substitute therefore with --N(14)--;

Claim 10, Col 132, line 50 delete "DNA:ASO-DNA" with --DNA:AGO-DNA--;

Claim 11, Col 132, line 55 delete "DNA:ASO-DNA" with --DNA:AGO-DNA--;

Claim 12, Col 132, line 59 between 'each type of' and 'in', insert --nucleic acid sequence triplex--;

UNITED STATES PATENT AND TRADEMARK OFFICE
CERTIFICATE OF CORRECTION

PATENT NO. : 5,856,103
DATED : January 5, 1999
INVENTOR(S) : DONALD M. GRAY

It is certified that error appears in the above-identified patent and that said Letters Patent is hereby corrected as shown below:

Claim 12, Col 132, line 61 delete "DNA:ASO-DNA" with --DNA:AGO-DNA--;

Claim 14, Col 134, line 3 delete "DNA:ASO-DNA" with --DNA:AGO-DNA-- and ;

Claim 15, Col 134, line 6 delete "DNA:ASO-DNA" with --DNA:AGO-DNA--.

Signed and Sealed this

Eighteenth Day of January, 2000

Attest:

Q. TODD DICKINSON

*Attesting Officer*       *Commissioner of Patents and Trademarks*

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ACGGGCCUCU CUUGCAAGGG CUAAGGU 27

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TGCCCGGAGA 10

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCCGGAGAG 10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCCGGAGAGA 10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCGGAGAGAA 10

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:6:

CGGAGAGAAC 10

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:7:

GGAGAGAACG 10

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

AGAGAGAGAG AGAGAGAGAG AGAG 24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

TCTCTCTCTC TCTCTCTCTC TCTC 24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:10:

UCUCUCUCUC UCUCUCUCUC UCUC 24

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

AGAGAGAGAG AGAGAGAGAG AGAG 24

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CCCCCACCAC TTCCCCTCTC     20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TGCCCATCAG GGCAGTTTGA     20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCTGTCCCGG GATAGGTTCA     20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CCCCCACCAC TTCCCCTCTC     20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GCCCAAGCTG GCATCCGTCA     20

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GACACTCAAT AAATAGCTGG T     21

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

TTGAGAAAGC TTTATTAACT 20

( 2 ) INFORMATION FOR SEQ ID NO:19:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

GGCTCCATTT CTTGCTCTCC 20

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CATTTCTTGC TCTCCTCTGT 20

( 2 ) INFORMATION FOR SEQ ID NO:21:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

GCTATGTCGA CACCCAATTC 20

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

CCGCCCCTCG CCTCTTGCCG 20

( 2 ) INFORMATION FOR SEQ ID NO:23:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

CGGGTCCCCT CGGGATTGGG 20

( 2 ) INFORMATION FOR SEQ ID NO:24:

( i ) SEQUENCE CHARACTERISTICS:

(A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:24:

CGGGTCCCCT CGGGATTGGG 20

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:25:

CACCTTCTTC TTCTATTCCT 20

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:26:

GAAGTCAGCC AAGAACAGCT 20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:27:

TATAGGAGTT TTGATGTGAA 20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:28:

CTGCTGCCTC TGTCTCAGGT 20

(2) INFORMATION FOR SEQ ID NO:29:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:29:

ACAGGATCTC TCAGGTGGGT 20

(2) INFORMATION FOR SEQ ID NO:30:

(i) SEQUENCE CHARACTERISTICS:
            (A) LENGTH: 21 base pairs
            (B) TYPE: nucleic acid ( C ) STRANDEDNESS: single
( D ) TOPOLOGY: linear ( x i ) SEQUENCE DESCRIPTION: SEQ ID NO:30:

AATCATGACT TCAAGAGTTC T                                                                 21

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TGAAGCAATC ATGACTTCAA G                                                                 21

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CCAAAGTGAG AGCTGAGAGA                                                                   20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

CTGATTCAAG GCTTTGGCAG                                                                   20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

TTCCCCAGAT GCACCTGTTT                                                                   20

( 2 ) INFORMATION FOR SEQ ID NO:35:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GACUAGCGGA GGCUAGAAGG AGAGAGAUGG GUGCGAGAGC GUCAGUAUUA AGCGGGGG               58

( 2 ) INFORMATION FOR SEQ ID NO:36:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (xi) SEQUENCE DESCRIPTION: SEQ ID NO:36:

TCTTCCTCTC TCTACCCACG CTCTC                             25

(2) INFORMATION FOR SEQ ID NO:37:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:37:

CCTCTCTCTA CCCACGCTCT CGCAG                             25